(12) United States Patent
Miller et al.

(10) Patent No.: US 11,129,545 B1
(45) Date of Patent: Sep. 28, 2021

(54) SYSTEMS AND METHODS FOR DETECTING ALCOHOL, ACETONE, AND CARBON MONOXIDE IN BREATH

(71) Applicant: University of South Florida, Tampa, FL (US)

(72) Inventors: Tiffany Crystal Miller, Tampa, FL (US); Salvatore Domenic Morgera, Tampa, FL (US); Stephen Edward Saddow, Tampa, FL (US); Arash Takshi, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 17/235,259

(22) Filed: Apr. 20, 2021

Related U.S. Application Data

(60) Provisional application No. 63/199,804, filed on Jan. 26, 2021, provisional application No. 63/198,666, filed on Nov. 2, 2020, provisional application No. 63/013,025, filed on Apr. 21, 2020.

(51) Int. Cl.
*A61B 5/08* (2006.01)
*A61B 5/00* (2006.01)
*A61B 5/097* (2006.01)

(52) U.S. Cl.
CPC .............. *A61B 5/082* (2013.01); *A61B 5/097* (2013.01); *A61B 5/4845* (2013.01)

(58) Field of Classification Search
CPC ........ A61B 5/082; A61B 5/097; A61B 5/4845
See application file for complete search history.

(56) References Cited

U.S. PATENT DOCUMENTS

| | | |
|---|---|---|
| 5,395,589 A | 3/1995 | Nacson |
| 6,837,095 B2 | 1/2005 | Sunshine et al. |
| 7,089,780 B2 | 8/2006 | Sunshine et al. |
| 8,485,983 B2 | 7/2013 | Gouma et al. |
| 8,758,261 B2 | 6/2014 | Gouma et al. |
| 8,955,367 B2 | 2/2015 | Gouma et al. |
| 2002/0177232 A1 | 11/2002 | Melker et al. |

(Continued)

OTHER PUBLICATIONS

Akaike et al., "Free Radicals in Viral Pathogenesis: Molecular Mechanisms Involving Superoxide and NO," Proceedings of the Nutrition Society, Jan. 1998, 217(1):64-73.

(Continued)

*Primary Examiner* — Eric J Messersmith
(74) *Attorney, Agent, or Firm* — Fish & Richardson P.C.

(57) ABSTRACT

A breath collection device can detect changes associated with pathogenesis of a disease, such as COVID-19, including biomarkers of immune response for respiratory symptoms, central nervous system injury, and/or peripheral nervous system injury in user breath and/or odor. The breath collection device can detect concentrations of alcohol, acetone, and carbon monoxide in user breath samples. A breath sample can be received in an internal bladder of the device for sensor analysis. Concentrations of alcohol, acetone, and carbon monoxide can be determined by calibrated calculation. A detection method for alcohol, acetone, and carbon monoxide can provide a non-invasive, rapid, and selective detection of gases in a variety of applications in virus detection as well as agricultural and homeland security.

20 Claims, 14 Drawing Sheets

(56) References Cited

U.S. PATENT DOCUMENTS

| | | | |
|---|---|---|---|
| 2004/0162500 A1* | 8/2004 | Kline | A61B 5/412 600/532 |
| 2013/0150746 A1* | 6/2013 | Tao | A61B 5/0836 600/531 |
| 2013/0239704 A1 | 9/2013 | Syage | |
| 2013/0253360 A1* | 9/2013 | Wang | G01N 33/0047 600/532 |
| 2014/0276100 A1* | 9/2014 | Satterfield | A61B 5/7271 600/476 |
| 2014/0358019 A1* | 12/2014 | Johnson | G01N 33/497 600/532 |
| 2015/0132858 A1* | 5/2015 | Ahmad | G01N 21/783 436/130 |
| 2016/0100774 A1* | 4/2016 | Wilcox | G16H 50/30 600/532 |
| 2016/0331272 A1* | 11/2016 | Ahmad | A61B 5/097 |
| 2019/0231222 A1* | 8/2019 | Ahmad | A61B 5/0836 |
| 2019/0282124 A1* | 9/2019 | Wu | A61B 5/0008 |
| 2020/0077923 A1* | 3/2020 | Wang | G01N 27/127 |
| 2020/0178891 A1* | 6/2020 | Verbeck, IV | A61B 5/087 |

OTHER PUBLICATIONS

Angle et al., "Real-time detection of a virus using detection dogs," Frontiers in veterinary science, Jan. 8, 2016, 2:79.

Angle et al., "Canine detection of the volatilome: A review of implications for pathogen and disease detection," Frontiers in veterinaiy science, Jun. 2016, 3:47.

Ashmawi et al., "Evaluation of lung cancer by estimating ferritin in exhaled breath condensate," Egyptian Journal of Chest Diseases and Tuberculosis, Apr. 1, 2015, 64(2):465-468.

Babizhayev et al., "Management of the Virulent Influenza Virus Infection by Oral Formulation of Nonhydrolized Carnosine and Isopeptide of Carnosine Attenuating Proinflammatory Cytokine-Induced Nitric Oxide Production," American Journal of Therapeutics, Jan. 2012, 19(l):e25-e47.

Banik et al., "Hydrogen sulphide in exhaled breath: a potential biomarker for small intestinal bacterial overgrowth in IBS," Journal of breath research, May 10, 2016, 10(2):026010, 9 pages.

Boesveldt et al., "Anosmia-A Clinical Review," Chemical Senses, May 22, 2017, 42(7):513-523.

Bruno et al., "Can the electronic nose diagnose chronic rhinosinusitis? A new experimental study," European Archives of Oto-Rhino-Laryngology, Jan. 8, 2008, 265(4):425-428.

Caruso et al. "Effect of short and long term gonadectomy on neuroactive steroid levels in the central and peripheral nervous system of male and female rats," Journal of neuroendocrinology, 2010, 22:11: 1137-1147.

Casaletto et al., "Retinal thinning is uniquely associated with medial temporal lobe atrophy in neurologically normal older adults," Neurobiology of aging, Mar. 1, 2017, 51: 15 pages.

Chen et al., "Breath-borne VOC Biomarkers for COVID-19," MedRxiv, Jun. 24, 2020, 11 pages.

Cheung et al. "Cytokine responses in severe acute respiratory syndrome coronavirus-infected macrophages in vitro: possible relevance to pathogenesis," Journal of virology, 2005, 79:12:7819-7826.

Cipollaro et al., "Musculoskeletal Symptoms in SARS-CoV-2 (COVID-19) Patients," Journal of Orthopaedic Surgery & Research, May 18, 2020, 15(1): 1-7.

Clerk, "A Treatise on Electricity and Magnetism," Oxford: Clarendon, 1892, 3rd ed., vol. 2., 12 pages.

Collins et al.,"Myelination of the developing lateral olfactory tract and anterior commissure," Journal of Comparative Neurology, Aug. 2018, 526:1843.

Craven et al., "The fluid dynamics of canine olfaction: Unique nasal airflow patterns as an explanation of macrosmia, " Journal of The Royal Society Interface, Jun. 2010, 7:47: 933-943.

Deluca et al. "Olfactory Pathology in Central Nervous System Demyelinating Diseases." Brain Pathology, Sep. 2015, 25:543.

Dong et al., "The role of imaging in the detection and management of COVID-19: a review," IEEE Reviews in Biomedical Engineering, 1-1, 14 pages.

Doty et al., "Assessment of the Portable C-320 Electronic Nose for Discrimination of Nine Insectivorous Bat Species: Implications for Monitoring White-Nose Syndrome," Biosensors, Feb. 2020, 10(2): 12, 26 pages.

Doty et al., "The influences of age on olfaction: a review," Front Psychol. 2014,5:20.

Fukushima et al., "Acetyl-1-Carnitine enhances myelination of regenerated fibers of the lateral olfactory tract, " Neuroscience Letters, Jul. 2017, 653: 215-219.

Galougahi et al. "Olfactory Bulb Magnetic Resonance Imaging in SARS-CoV-2-Induced Anosmia: The First Report," Academic radiology, Apr. 2020, S1076-6332(20)30194-X, 2 pages.

Gao et al., "A novel fingerprint map of SARS-CoV with visualization analysis," Third International Conference on Image and Graphics (ICIG'04), Hong Kong, China, Dec. 2004, 226-229.

Garcia-Gonzalez et al., "Olfactory system and demyelination," The Anatomical Record, Sep. 2013, 296(9): 1424-1434.

Germanese et al., "An E-Nose for the Monitoring of Severe Liver Impairment: A Preliminary Study," Sensors, Sep. 2019, 19(17):3656, 16 pages.

Gongora et al., "An Electronic Architecture for Multipurpose Artificial Noses," Journal of Sensors, Feb. 2018, 9 pages.

Gouma et al., "Gas Sensor with Compensations for Baseline Variations," 20150217 2015.

Gouma et al., "Novel Isoprene Sensor for a Flu Virus Breath Monitor," Sensors, Jan. 2017, 17(1)499, 7 pages.

Gui et al., "Cryo-electron microscopy structures of the SARS-CoV spike glycoprotein reveal a prerequisite conformational state for receptor binding," Cell research, Jan. 2017, 27(1): 119-129.

Hartman et al., "COVID-19 Respiratory Failure: Targeting Inflammation on VV-ECMO Support," ASAIO Journal, May 11, 2020, 66(6):603-606, 4 pages.

He et al., "Expression of elevated levels of pro-inflammatory cytokines in SARS-CoV-infected ACE2+ cells in SARS patients: relation to the acute lung injury and pathogenesis of SARS," The Journal of Pathology, Oct. 9, 2006, 210:288-297.

Henderson et al., "A benchmarking protocol for breath analysis: the peppermint experiment," Journal of Breath Research, Jul. 31, 2020, 14(4):1-10.

Hideshima et al., "Glycan-immobilized dual-channel field effect transistor biosensor for the rapid identification of pandemic influenza viral particles," Scientific reports, Aug. 12, 2019, 9(1): 1-10.

Hoffmann et al., "Priming Time: How Cellular Proteases Arm Coronavirus Spike Proteins," Activation of Viruses by Host Proteases, Feb. 2018, 71-98.

Hui-Ling et al. "SARS-CoV-2 Viral Load in upper respiratory specimens of infected patients." New England Journal of Medicine, Mar. 2020, 382:1177-1179.

Hurot et al., "Bio-Inspired Strategies for Improving the Selectivity and Sensitivity of Artificial Noses: A Review," Sensors, Mar. 2020, 20(6): 1803, 28 pages.

Hussain et al., "Structural variations in human ACE2 may influence its binding with SARS-CoV-2 spike protein," J Med Virol,, Apr. 2020, 17 pages.

Iravani et al., "Non-invasive recording from the human olfactory bulb," Nature communications, Jan. 31, 2020, 11(1): 1-10.

Jeong-Min et al. "Identification of Coronavirus Isolated from a Patient in Korea with COVID-19,"Osong public health and research perspectives, 2020, 11:1:3-7.

Joseph et al., "Back on the Scent: The Olfactory System in CNS Demyelinating Diseases." Journal of Neurology, Neurosurgery & Psychiatry, Oct. 2016, 87(10): 1146-1154.

Karimi et al., "Single Exhale Biomarker Breathalyzer," Sensors, Jan. 2019, 19(2):270, 11 pages.

Konstantinidi et al., "Exhaled breath condensate: technical and diagnostic aspects," The Scientific World Journal, Oct. 2015, 2015:1-26.

(56) References Cited

OTHER PUBLICATIONS

Kremer et al. "Brain MRI findings in severe COVID-19: A Retrospective Observational Study, " Radiological Society of North America, 2020, 202222, 18 pages.

Lewis et al., "Identifying Volatile Metabolite Signatures for the Diagnosis of Bacterial Respiratory Tract Infection Using Electronic Nose Technology: A Pilot Study," PLoS ONE, Dec. 2017, 12(12):1-10.

Liu et al., "Research and Development on Therapeutic Agents and Vaccines for COVID-19 and Related Human Coronavirus Diseases," ACS Central Science, 2020, 6(3):315-331, 17 pages.

Lundberg, "Airborne nitric oxide: inflammatory marker and aerocrine messenger in man," Acta Physiologica Scandinavica Suppiementum, Jan. 1, 1996, 633:1-27.

Marinosci et al., "Possible link between anosmia and COVID-19: sniffing out the truth," European Archives of Oto-Rhino-Laryngology, Apr. 17, 2020, 277:2149-2150.

Miekisch et al., "Diagnostic potential of breath analysis—focus on volatile organic compounds," Clinica Chimica Acta, Sep. 2004, 347(l-3):25-39.

Millet et al., "Cytokine contributions to alterations of the volatile metabolome induced by inflammation," Brain Behavior and Immunity, 2018, 69:312-320.

Mohamed et al., "A novel method for diagnosing chronic rhinosinusitis based on an electronic nose," Anales Otorrinolaringologicos Iberoamericanos, Jan. 1, 2003, 30(5):447-457.

Molloy et al., "COVID-19 in children and altered inflammatory responses," Pediatric Research, Apr. 3, 2020, 88:340-341.

Montalvan et al., "Neurological manifestations of COVID-19 and other coronavirus infections: A systematic review," Clinical neurology and neurosurgery, 2020, 194:105921.

Moriguchi, et al. "A First Case of Meningitis/Encephalitis Associated with SARS-Coronavirus-2,"International Journal of Infectious Diseases, May 2020, 94:.55-58, doi:10.1016/j.ijid.2020.03.062.

Neuroanatomy.wisc.edu.[online] "Olfactory Pathways and Limbic System," retrieved on Jun. 15, 2021, retrieved from URL<http://www.neuroanatomy.wisc.edu/coursebook/neuro3(2).pdf,> 12 pages.

Olsson et al., "The Scent of Disease: Human Body Odor Contains an Early Chemosensory Cue of Sickness," Psychological Science, Jan. 22, 2014, 25(3):817, 7 pages.

Ortega et al., "Role of changes in SARS-CoV-2 spike protein in the interaction with the human ACE2 receptor: Aninsilico analysis," EXCLI journal, 2020, 19:410-417.

Palao et al.," Multiple Sclerosis following SARS-CoV-2 infection, Multiple Sclerosis and Related Disorders," Jul. 2020, 102377:doi: https://doi.Org/10.1016/j.msard.2020.102377.

Paterson et al., "The emerging spectrum of COVID-19 neurology: clinical, radiological and laboratory findings," Brain, 2020, 36 pages.

Pellitero et al., "Paciente con clinica neurologica comounica manifestacion de infeccin por SARS-CoV-2," Nemologia, 2020, 35:271 272.

Persaud, "Towards bionic noses," Sensor Review, Mar. 20, 2017, 37(2): 165-171, 15 pages.

Princivalle et al., "Pancreatic ductal adenocarcinoma can be detected by analysis of volatile organic compounds (VOCs) in alveolar air," BMC cancer, Dec. 2018, 18(1): 1-10.

Punetha et al., "Ultrafast and Highly Selective CO Gas Sensor Based on RGO/Fe304 Nanocomposite at Room Temperature," 2019 IEEE Sensors, Oct. 27-30, 2019, 4 pages.

Qiu et al., "Dual-functional plasmonic photothermal biosensors for highly accurate severe acute respiratoiy syndrome coronavirus 2 detection," ACS nano, Apr. 13, 2020, 14(5):5268-5277.

Ramos et al., "Neurology during the pandemic. Is COVID-19 changing the organisation of neurology departments?" Nemologia (EnglishEdition), 2020, 35:4: 269-271.

Ren et al. "Association of the Insulin Resistance Marker TyG Index with the Severity and Mortality of COVID-19," May 2020, Cardiovascular Diabetology, 19:58.

Rodriguez-Aguilar et al., "Ultrafast Gas Chromatography Coupled to Electronic Nose to Identify Volatile Biomarkers in Exhaled Breath from Chronic Obstructive Pulmonary Disease Patients: A Pilot Study," Biomedical Chromatography, Aug. 19, 2019, 12, 10 pages.

Rodriguez-Aguilarr et al., "Ultrafast Gas Chromatography Coupled to Electronic Nose to Identify Volatile Biomarkers in Exhaled Breath from Chronic Obstructive Pulmonary Disease Patients: A Pilot Study," Biomedical Chromatography, 2019, 12.

Roper, "Gustatory and Olfactory Sensory Transduction," Cell Physiology Source Book (Fourth Edition), Sperelakis et al. (eds.), 2012, Chapter 39:681-697.

Ruszkiewicz et al., "Diagnosis of COVID-19 by analysis of breath with gas chromatography-ion mobility spectrometry-a feasibility study," EClinicalMedicine, Dec. 1, 2020, 29:100609, 10 pages.

Ryan et al., "Monitoring Space Shuttle Air Quality Using the Jet Propulsion Laboratory Electronic Nose," IEEE Sensors Journal, Jun. 2004, 4(3):337-347.

Saito et al., "Field-deployable rapid multiple biosensing system for detection of chemical and biological warfare agents," Microsystems and Nanoengineering, Jan. 29, 2018, 4:17083, 11 pages.

Seo et al., "Rapid Detection of COVID-19 Causative Virus (SARS-CoV-2) in Human Nasopharyngeal Swab Specimens Using Field-Effect Transistor-Based Biosensor," ACS Nano, Apr. 15, 2020, 14(4):5135-5142.

Sethi et al. "Clinical application of volatile organic compound analysis for detecting infectious diseases." Clinical microbiology reviews, 2013, 26:3:462-75.

Sethi et al., "Clinical Application of Volatile Organic Compound Analysis for Detecting Infectious Diseases," Clinical Microbiology Reviews, Jul. 2013, 26(3):462-475.

Shehada et al., "Silicon nanowire sensors enable diagnosis of patients via exhaled breath.," ACS nano, Jul. 26, 2016, 10(7):7047-7057.

Shin, "Medical applications of breath hydrogen measurements," Analytical and bioanalytical chemistry, Jun. 2014, 406(16):3931-3939.

Skarysz et al., "Fast and automated biomarker detection in breath samples with machine learning," May 24, 2020, arXiv preprint arXiv:2006.01772, 26 pages.

Smith et al., "Anatomy of the olfactory system," Handbook of Clinical Neurology, Doty (ed.), 2019, Chapter 2, 164:17-28.

StatPearls.com [online], "Features, evaluation, and treatment coronavirus (COVID-19)," Updated Apr. 20, 2021, retrieved Jun. 15, 2021, retrieved from URL <https://www.statpearls.com/ArticleLibrary/viewarticle/52171>, 29 pages.

Stefano et al., "Potential Immunoregulatory and Antiviral/SARS-CoV-2 Activities of Nitric Oxide," Medical Science Monitor, May 2020, 26:e925679, 3 pages.

Sungnak et al., "SARS-CoV-2 Entry Factors Are Highly Expressed in Nasal Epithelial Cells Together with Innate Immune Genes," Nature Medicine, May 2020, 26:681-687.

Toscano et al.,"Guillain-Barre Syndrome Associated with SARS-CoV-2," New England Journal of Medicine, Jun. 2020, 382:26:2574 2576.

Vaduganathan, et al., "Renin-Angiotensin-Aldosterone System Inhibitors in Patients with Covid-19," The New England Journal of Medicine, Apr. 2020, 7 pages.

Van Riel et al., "The olfactory nerve: a shortcut for influenza and other viral diseases into the central nervous system," The Journal of Pathology, 2015, 235:277-287.

Vargas-Vargas et al., "Ferritin levels and COVID-19," Rev Panam Salud Publica. 2020;44: 2 pages.

Vashist, "In vitro diagnostic assays for COVID-19: recent advances and emerging trends," Diagnostics, Apr. 2020, 10(4): 202, 7 pages.

Vlasic et al., "Iron and Ferritin Concentrations in Exhaled Breath Condensate of Children with Asthma," Journal of Asthma, 2009,46(1), 81-85.

Voss et al., "The e-nose prototype to monitoring the growth and maturation of peaches in the orchard," IEEE Sensors Journal, Oct. 15, 2020, 20(20):11741-11750, 10 pages.

Walls et al., "Structure, function, and antigenicity of the SARS-CoV-2 spike glycoprotein," Cell, Apr. 16, 2020, 181(2):281-292.

(56) References Cited

OTHER PUBLICATIONS

Walt et al., "Artificial Noses," American Scientist, Jan.-Feb. 2012, 100(1): 9 pages.

Wang et al., "Structural and Functional Basis of SARS-CoV-2 Entry by Using Human ACE2," Cell, May 2020, 181(4):894-904, 21 pages.

Wang et al., "Clinical manifestations and evidence of neurological involvement in 2019 novel coronavirus SARS-CoV-2: a systematic review and meta-analysis," Journal of neurology, Jun. 2020, 13 pages.

Wang, "Combination of Serological Total Antibody and RT-PCR Test for Detection of SARS-COV-2 Infections," Journal of Virological Methods, Sep. 2020, 283:113919, 4 pages.

Waxman, "Axonal conduction and injury in multiple sclerosis: the role of sodium channels," Nat. Rev. Neuroscience, 2006, 12:932-941.

Wenig, "Undifferentiated malignant neoplasms of the sinonasal tract," Archives of pathology & laboratoiy medicine, May 2009, 133(5):699-712.

Wilson et al., "Advances in Electronic-Nose Technologies Developed for Biomedical Applications." Sensors, Jan. 2011, 11(1):1105-1176.

Wilson, "Advances in Electronic-Nose Technologies for the Detection of Volatile Biomarker Metabolites in the Human Breath," Metabolites, Mar. 2015, 5(1): 140-163.

Zamuruyev et al. "Human breath metabolomics using an optimized non-invasive exhaled breath condensate sampler," Journal of breath research, Dec. 2016, 11:1: 016001.

Zhou et al., "Effect of Gastrointestinal Symptoms in Patients With COVID-19," Gastroenterology, Jun. 2020, 158(8):2294-2297.

Zimmerpeacocktech.com [online], "The detection of COVID-19 on the breath followed by PCR," 2020, retrieved Jun. 24, 2021, retrieved from URL<https://www.zimmerpeacocktech.com/products/electrochemical-sensors/covid-19-and-pcr-on-the-breath>, 2 pages.

Rose-Pehrsson et al., "Trace Vapor Generator for Explosives and Narcotics (TV-GEN)," Naval Research Lab Washington DC, Dec. 12, 2018, 49 pages.

\* cited by examiner

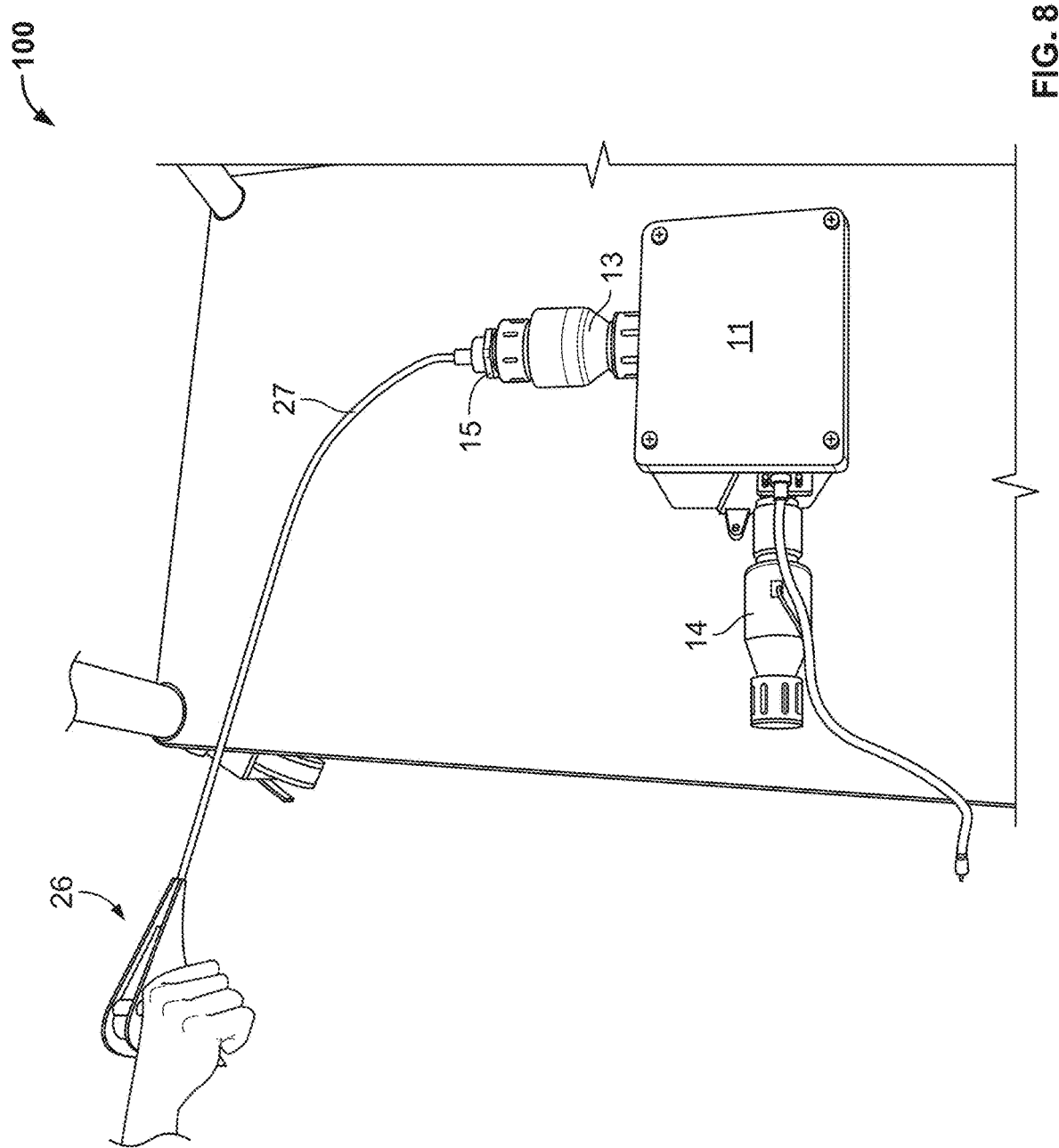

SYSTEMS AND METHODS FOR DETECTING ALCOHOL, ACETONE, AND CARBON MONOXIDE IN BREATH

CROSS-REFERENCE TO RELATED APPLICATION

This application claims priority to U.S. Provisional Patent Application No. 63/013,025, filed on Apr. 21, 2020, U.S. Provisional Patent Application No. 63/198,666, filed on Nov. 2, 2020 and U.S. Provisional Patent Application No. 63/199,804, filed on Jan. 26, 2021, all of which are incorporated herein by reference in their entirety.

TECHNICAL FIELD

This document describes devices, systems, and methods related to systems and methods for detecting concentrations of gases in an individual's breath. More particularly, this document generally describes detecting SARS-CoV-2 biomarkers in the individual's breath to identify whether the individual is infected with COVID-19.

BACKGROUND

Contagious diseases can rapidly spread amongst populations. Sometimes, the spread of such diseases can go unnoticed. Sometimes, the spread of such diseases can be noticed too late. Diseases such as COVID-19 are rapidly changing. Diagnostic testing of individuals for COVID-19 can facilitate removal of infected individuals from the population. By removing the infected individuals, COVID-19 can spread more slowly to others in the population.

Some COVID-19 diagnostic RNA testing methods, such as polymerase chain reaction (PCR), can require use of swabs and reagents. During periods of high demand, such as during a national pandemic, these materials can be in short supply. As a result, it can be challenging to test large populations of individuals at a time and isolate infected individuals before they spread COVID-19 to others. Moreover, PCR testing can have a higher than desirable false negative rate. Infected individuals may not be identified or isolated before they spread the disease to others in the population.

Many commercially available biosensors use electrochemical cells for detection. In electrochemical detection methods, an electrode must be exposed to a solution containing a target biomolecule and wait for incubation. Such methods can cause a delay in identifying whether an individual is infected. Sniffing detection methods for air quality (such as the JPL eNose or Cyranose) may involve modeling and thus may not be conducive to rapid diagnostic testing for diseases such as COVID-19. Antibody testing can also be used. However, antibody testing can be an invasive form of detection that is valuable for individuals who recovered from the disease but not for diagnosis.

SUMMARY

The document generally describes systems and methods for detecting concentrations of gases in an individual's breath. The disclosed technology can provide for a breath collection device capable of diagnostic point-of-care testing of individuals' breaths for rapid diagnosis of diseases such as COVID-19. In particular, the disclosed technology can detect SARS-CoV-2 biomarkers in an individual's breath to determine whether the individual is infected with COVID-19. The SARS-CoV-2 Spike 1 (S1) protein can dock at human cell membrane protein angiotensin-converting enzyme 2 (ACE2) during infection. The disclosed technology can therefore include sensors configured to detect carbon monoxide, ethanol, hydrogen, ammonia, and/or methane (solvents). The disclosed technology can also provide for attachment of a solvent molecule tag to a cultured S1 protein. The tag can have a first end being the ACE2 protein to facilitate bridging to the S1 protein and a second end having a chosen solvent to be detected. The disclosed technology can therefore be configured to detect the S1 protein of the Coronavirus family.

The disclosed breath collection device can include a micro-pump intake, a low-noise electronic circuit design, specific and sensitive detection arrays, and digital signal processing methods. The disclosed technology can minimize need for additional materials, equipment, and time needed to accurately diagnose COVID-19 infected individuals. Nano-film sensor arrays can be configured in the device to detect direct, unaltered, and/or labeled Coronavirus proteins and associated inflammatory biomarkers. The nano-film sensor arrays can have associated nucelocapsid proteins configured for a high binding affinity for leader sequences of viral genomes. This binding affinity can influence a reactive electronic element of the disclosed device, which in turn can create a signal that can be used to detect a plurality of Coronavirus types. The device can also include nanotechnology-based biosensors that can show a high specificity and sensitivity after labeling with an NA probe, antibody, and/or other specific molecules with affinity to a target structure. The disclosed device can also include the low-noise electronic circuit design to connect to the sensor arrays and perform signal conditioning, data acquisition (A/D conversion), digital signal processing, and pattern recognition techniques and methods.

Particular embodiments described herein include a breath collection system for sensing an infectious disease. The system can include a housing having a chamber located therein and a first check valve attached to the housing and in fluid communication with the chamber. The first check valve can receive a breath sample from a user. The system can also have a second check valve attached to the housing and in fluid communication with the chamber. The second check valve can expel the breath sample from the chamber. The chamber can house an internal bladder in fluid communication with the first check valve and the second check valve, and a plurality of sensors positioned at least partially within the internal bladder. The plurality of sensors can detect one or more VOC signatures in the breath sample. The chamber can also house a microcontroller in electrical communication with the plurality of sensors. The microcontroller can classify, based on the detected VOC signatures in the breath sample, the breath sample.

In some implementations, the system can optionally include one or more of the following features. For example, the system can also include at least one mucin gel layer configured to overlay at least one of the plurality of sensors. The one mucin gel layer can resemble a nasal cavity of a user. The at least one mucin gel layer can also include a plurality of pores through which a plurality of synthetic hair-like projections radiate therefrom.

The system can also include a plurality of synthetic hair-like projections that radiate from an inner wall surface of the internal bladder. Moreover, the system can include a mucus dispensing mechanism housed within the chamber. The mucus dispensing mechanism can inject a predetermined quantity of mucin-based gel into the chamber. The mucin-based gel can cover at least a portion of the plurality of synthetic hair-like projections and the inner wall surface of the internal bladder.

As another example, the system can include UVC germicidal LEDs housed within the chamber. The UVC germicidal LEDs can, when actuated, remove bacteria from within the internal bladder. In some implementations, the system can also include a filtration system attached to the second check valve that can purify air that is purged from within the internal bladder. The system can also include a compressed air device having a hose. The hose can attach to the first check valve and inject compressed air into the internal bladder. The system can also include a mouthpiece removably attached to and in fluid communication with the first check valve. The mouthpiece can receive a mouth of the user.

In some implementations, at least one of the plurality of sensors can detect gas concentrations in parts per million of at least one of carbon monoxide, acetone, or alcohol. In some implementations, the system can also include a facemask having a mouthpiece. The facemask can be worn by the user and the mouthpiece can receive breath from the user. The mouthpiece can be in fluid communication with the first check valve. Moreover, in some implementations, the at least one mucin gel layer can be an electroconductive hydrogel derived from jelly of Ampullae of Lorenzini.

Particular embodiments described herein can also include methods for detecting VOC signatures indicative of an infectious disease in a breath sample. The method can include receiving the breath sample via a mouthpiece in fluid communication with a first check valve in a breath collection device, and activating mucin-based gel secretion in a chamber housed within the breath collection device. The mucin-based gel can coat at least a portion of an interior wall surface of the chamber. The method can also include detecting, by one or more sensors housed in the chamber, VOC signatures in the breath sample, classifying, based on the VOC signatures exceeding threshold levels, the breath sample as infected, and expelling the breath sample through a second check valve in the breath collection device.

In some implementations, the method can optionally include one or more additional features. For example, the method can include removing the mouthpiece from the first check valve, attaching an air compressor to the first check valve, and injecting compressed air from the air compressor into the chamber of the breath collection device. The compressed air can push the breath sample out through the second check valve in the breath collection device.

The method can also include activating UVC germicidal LEDs within the chamber to remove bacteria from within the chamber.

Particular embodiments described herein can also include a diagnostic system for sensing viruses. The system can include a breath collection device having a housing. The housing can include at least a portion of a removable mask that can overlay a mouth and a nose of a user, a collection element that is retained by a support structure of an inner wall surface of the removable mask portion, an intake pump that can guide aerosols from the removable mask portion to the collection element, a pressure sensor in electrical communication with the intake pump, a gas sensor that can detect gas concentrations in the aerosols, and a layer of porous film that can overlay the gas sensor.

In some implementations the system can include one or more of the following features. For example, the collection element can have an inner wall surface that can include at least a portion of a nanofilm having at least one receptor. The at least a portion of the nanofilm can be magnetic. In some implementations, the at least one receptor can be at least one of (i) angiotensin-converting enzyme 2 and (ii) liver and lymph node sinusoidal endothelial cell c-type lectin. As another example, a first receptor of the at least one receptor can be angiotensin-converting enzyme 2 and a second receptor of the at least one receptor can be liver and lymph node sinusoidal endothelial cell c-type lectin. In some implementations, the layer of porous film can be at least one of (i) an electroconductive hydrogel derived from jelly of Ampullae of Lorenzini and (ii) a mucin-based gel.

The devices, system, and techniques described herein may provide one or more of the following advantages. For example, the disclosed technology can provide for slowing a spread of contagious diseases, such as COVID-19, with rapid signal indication. The disclosed technology can detect changes associated with pathogenesis of a disease, such as biomarkers of immune response for respiratory symptoms, central nervous system injury, and/or peripheral nervous system injury in the breath and/or odor of an individual. These changes can be quickly detected and outputted, which can be beneficial to slow the spread of infectious diseases. The disclosed technology can serve as a noninvasive, point-of-care, low-cost diagnostic screening method for respiratory diseases including, but not limited to, SARS-CoV and SARS-CoV-2, which causes COVID-19. The disclosed technology can improve public health as a result of providing accurate and almost instant detection of COVID-19.

As another example, the disclosed technology can minimize need for additional materials, equipment, and time needed to accurately diagnose disease-infected individuals. The disclosed technology can provide for a moveable breath collection device that houses sensors and a microcontroller configured to process a breath sample and identify gas concentrations in the breath sample. Since breath analysis and processing can be performed at the device, the individual can be more quickly diagnosed as infected or not infected. The disclosed technology eliminates a need for using an electrochemical cell, so detection response time can be faster as an incubation period is not needed. Moreover, since the disclosed technology does not require use of swabs and/or reagents, the disclosed technology can be more easily and quickly deployed in situations where mass testing is needed. The disclosed technology can also be less expensive to deploy since the disclosed technology does not require additional, auxiliary equipment and/or materials for effective diagnostics.

As another example, the disclosed technology can include cilia-like projections and a mucin gel layer within a bladder where the user breath flows. The projections and mucin gel layer can mimic a nasal cavity of the user. Therefore, when the user breath flows through the projects and mucin gel layer, gas sensors can be more selective and accurate in detecting target gasses.

The details of one or more implementations are set forth in the accompanying drawings and the description below. Other features and advantages will be apparent from the description and drawings, and from the claims.

BRIEF DESCRIPTION OF THE DRAWINGS

FIG. 8 depicts a sterilization procedure for the breath collection device.

Like reference symbols in the various drawings indicate like elements.

DETAILED DESCRIPTION OF ILLUSTRATIVE EMBODIMENTS

This document generally describes systems and methods for a non-invasive electronic nose sniffing approach to detect disease biomarkers in user breath. For example, using nano-film sensors, a biomarker of COVID-19 can be detected in the user's breath. The user can be quickly diagnosed with COVID-19 in an effort to slow the spread of COVID-19 to others in a population. The disclosed technology tests breath of the user through air sample analysis and serves as a noninvasive, point-of-care, low-cost diagnostic screening method for respiratory diseases including, but not limited to, SARS-CoV and SARS-CoV-2, which cause COVID-19. The disclosed technology also provides for attaching a solvent molecule tag to a cultured S1 protein.

Figure 1A:
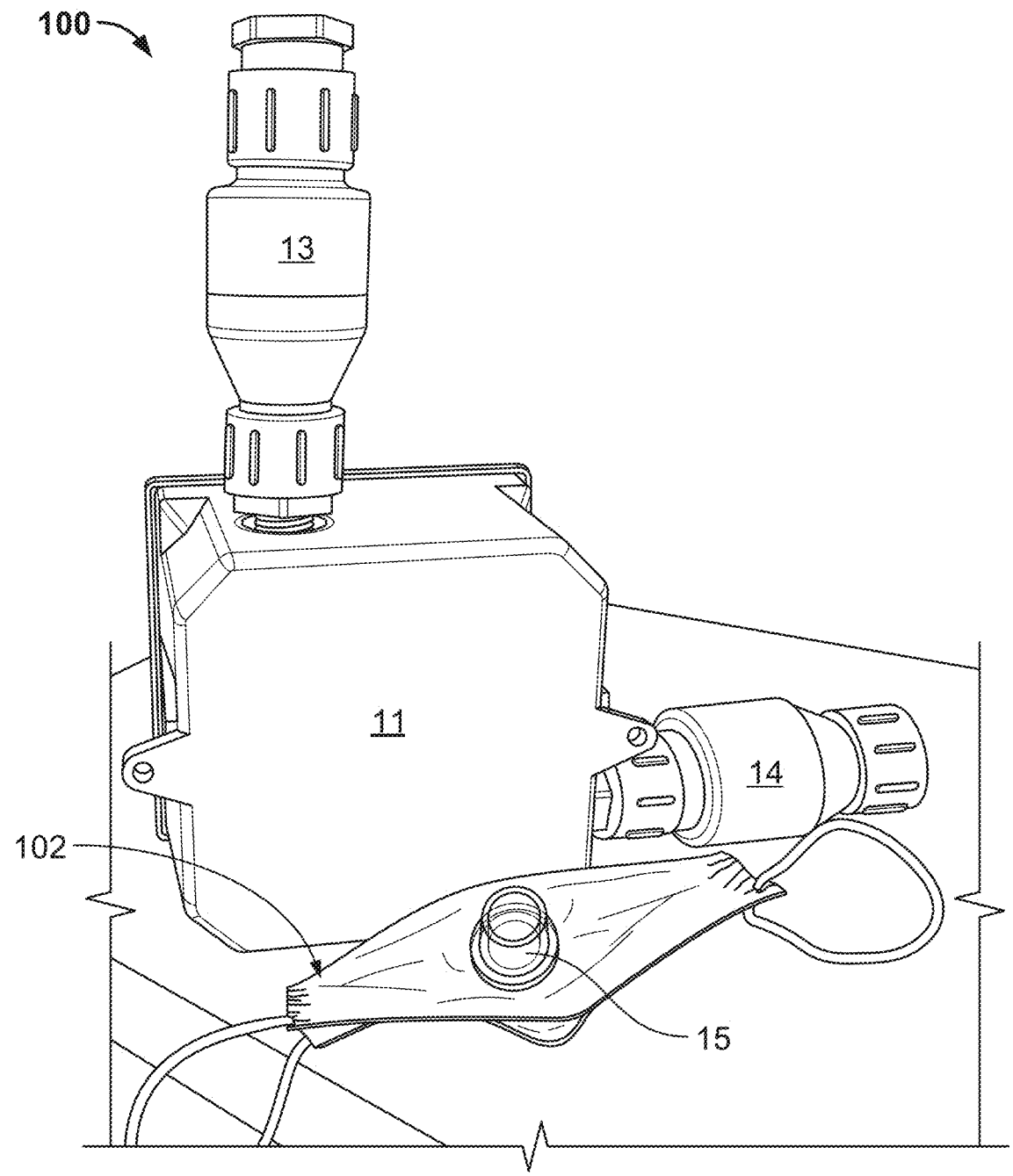
FIG. 1A is a front perspective view of a breath collection device as described herein.
Figure 1B:
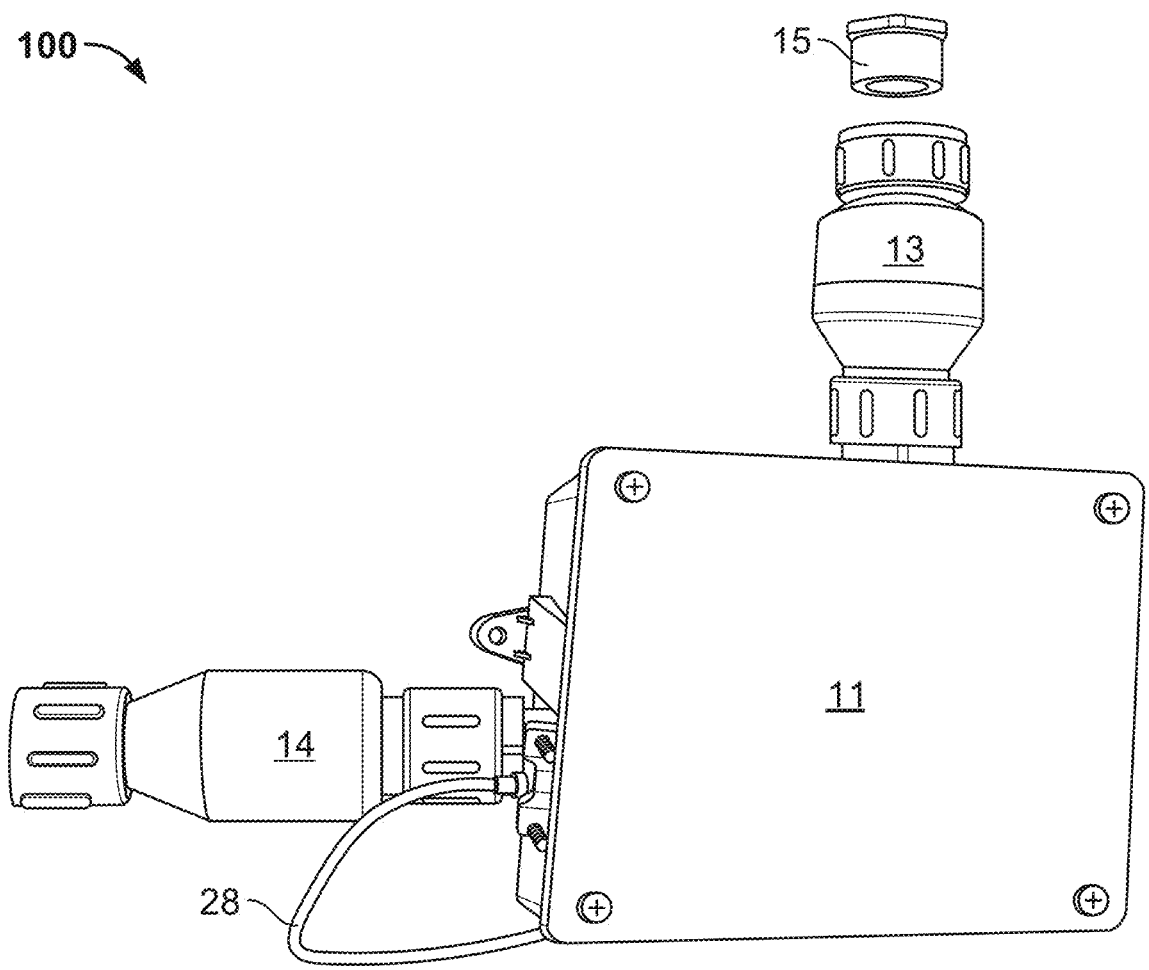
FIG. 1B is a rear plain view of the breath collection device.

Referring to the figures, FIG. 1A is a front perspective view of a breath collection device 100 as described herein. FIG. 1B is a rear plain view of the breath collection device 100. Referring to both FIGS. 1A-B, the breath collection device 100 can be configured to detect, from a user's exhaled breath, a variety of gasses like acetone, hydrogen, NO, alcohol, and carbon monoxide that can be indicators of disease-related infection and symptoms. As described in further detail below, a sample of the user's breath can be collected in a chamber where gas sensors can detect voltage changes when the sensors contact a COVID-19 gas in the breath sample. These voltage changes can be stored in a computer database. A resulting pattern can be identified from the voltage changes. The pattern can be a signature of COVID-19. For example, the disclosed technology can determine a volatile organic compound (VOC) signature of respiratory/neurological diseases such as COVID-19 from a plurality of exhaled biomarkers over time. A predetermined sampling protocol can also be used to minimize contamination of samples. A mucus film can be applied to the sensors of the device 100 to provide a rapid, accurate, sensitive, selective detection of VOCs, such as the aforementioned, hydrogen, CO, NO, Alcohol, and Acetone that are associated with some symptoms of COVID-19. Thus, the disclosed device 100 can be used for detecting levels of VOCs specific to SARS-CoV-2.

Referring to the breath collection device 100 in FIGS. 1A-B, the device 100 has a first check valve 13, a second check valve 14, a housing 11, and an electrical connection 28. The valves 13 and 14 can be one-way valves. The first check valve 13 located at a top of the housing 11 (e.g., vessel) allows exhaled breath to enter a collection chamber within the housing 11. The breath can flow through the collection chamber positioned between the first and second check valves 13 and 14. As the breath flows through the collection chambers, sensors can collect information about the breath that can be used to detect VOC levels in the user's breath. Power can be provided to the sensors and other components in the device 100 via the electrical connection 28. For example, the electrical connection 28 can be coupled to a power source such as a battery or power outlet.

The breath can escape the collection chamber via the second check valve 14. As a result, the collection chamber can be purged of the encased exhaled breath. Once the exhaled breath escapes the collection chamber, the breath collection device 100 can be used to diagnose another user's breath sample.

A user can breathe into the first check valve 13 via a mouthpiece 15. As shown in FIG. 1A, the mouthpiece 15 can be attached to a facemask 102. As a result, the user may not have to remove their facemask 102 in order to breathe into the device 100. The facemask 102 can be configured with an opening over a portion of the facemask 102 that covers the user's mouth. The mouthpiece 15 can then be inserted or otherwise attached to the opening in the facemask 102. When the user breathes while wearing the facemask 102, the user's breath can travel through the mouthpiece 15 and into the first check valve 13.

In some implementations, the mouthpiece 15 can be directly attached to the first check valve 13 instead of the facemask 102 (e.g., refer to FIG. 1B). The user can then breathe directly into the first check valve 13 using the mouthpiece 15. The mouthpiece 15 can be removable and disposable. For example, a new mouthpiece 15 can be attached to the first check valve 13 for each new user. In some implementations, the mouthpiece 15 can also be removed, sanitized, and then attached to the first check valve 13 before use by each new user. The mouthpiece 15 can be a 1" to ¾" reducer bushing.

FIG. 2A is a cross-sectional view of the breath collection device 100. The device 100 includes the housing 11, first check valve 13, second check valve 14, electrical connection 28, a chamber 31 within the housing 11, an optional breath sample vessel 32, internal bladder 16, circuitry 18, and sensors 6A-C. User breath can flow 22 through the first check valve 13 and into the chamber 31.

A flowmeter (not depicted) can also be configured to the collection device 100 to adjust the breath flow 22 rate to approximately 25.00 mL/s. As the flow rate increases, detection time of one or more of the sensors 6A-C can decrease, which can be more desirable for rapid detection of target gasses. Output responses of the sensors 6A-C demonstrate an elevated output response as a result of an increased flow for concentrations of breath between 10 ppm-300 ppm. Concentrations in ppm of alcohol, carbon monoxide, and acetone can be calculated after the output of the sensors 6A-C are converted by a microcontroller of the device 100.

The breath can continue to flow 23 through the internal bladder 16 before being expelled through the second check valve 14. A t-handle of the second check valve 14 can be oriented in a closed position to ensure the user breath remains within the internal bladder 16 long enough to saturate one or more of the gas sensors 6A-C. The breath can flow 23 to the sensors 6A-C, which can be mounted on an inner wall surface of the internal bladder 16 near the first check valve 13. The breath can then be exhausted through the second check valve 14 when the t-handle of the valve 14 is oriented in an open position. Thus, the internal bladder 16 can be connected to both the first check valve 13 and the second check valve 14. The internal bladder 16 can separate the circuitry 18 from gasses obtained from the user's breath, whereby, at least a portion of the sensors 6A-C can be retained within the internal bladder 16.

One or more of the sensors 6A-C can be temperature and/or pressure sensors (e.g., BME280 sensor) that can be retained inside (or partially inside) the interior bladder 16 and configured to measure temperature and pressure of the breath flow 23 and/or the chamber 31 of the housing 11. One or more of the sensors 6A-C can also be gas sensors that are configured to receive indications that the breath's temperature is within a certain predetermined range. Upon receiving such indications, the gas sensors can detect levels of gasses, such as alcohol, acetone, and carbon monoxide, in the user's breath. One or more of the gas sensors 6A-C can be MQ-2 and/or MQ-135 sensors. In some implementations, an array of metal-oxide semiconductor (MOS) gas sensors (e.g., sensors 6A-C) can be retained in the chamber 31 of the housing 11. These sensors can be saturated by a target gas to then produce a voltage drop across the sensors that results in an output response in volts (V). After gasses emitted from the breath saturate the sensors 6A-C, an analog signal from the sensors 6A-C can be transmitted to a comparator configured to digitize the signal. The comparator can determine when threshold values set by a potentiometer of the sensors have been met. The comparator can be part of the circuitry 18.

The MOS-based sensors can detect gas concentrations in parts-per-million (ppm) of carbon monoxide, acetone, and alcohol. The sensors 6A-C can be positioned along the breath flow 23 such that the breath passes the MQ-2 sensor configured to detect carbon monoxide and alcohol, the MOS-based MQ-135 sensor configured to detect acetone, and the BME280 sensor configured to detect temperature having a BMP280 piezo-resistive pressure sensor.

The circuitry 18 can include a microcontroller configured to control one or more of the components described in reference to the breath collection device 100. The circuitry 18 can electrically connect MOS-based MQ-2 and MQ-138 gas sensors and/or an electrochemical SGX-4NO-250 gas sensor (e.g., the sensors 6A-C) to the microcontroller. The circuitry 18 and/or the electrical connection can also connect the sensors 6A-C a power source (e.g., 5V battery). The electrical connection 28 can also provide communication between the breath collection device 100 and a user computing device or system.

Figure 2A:
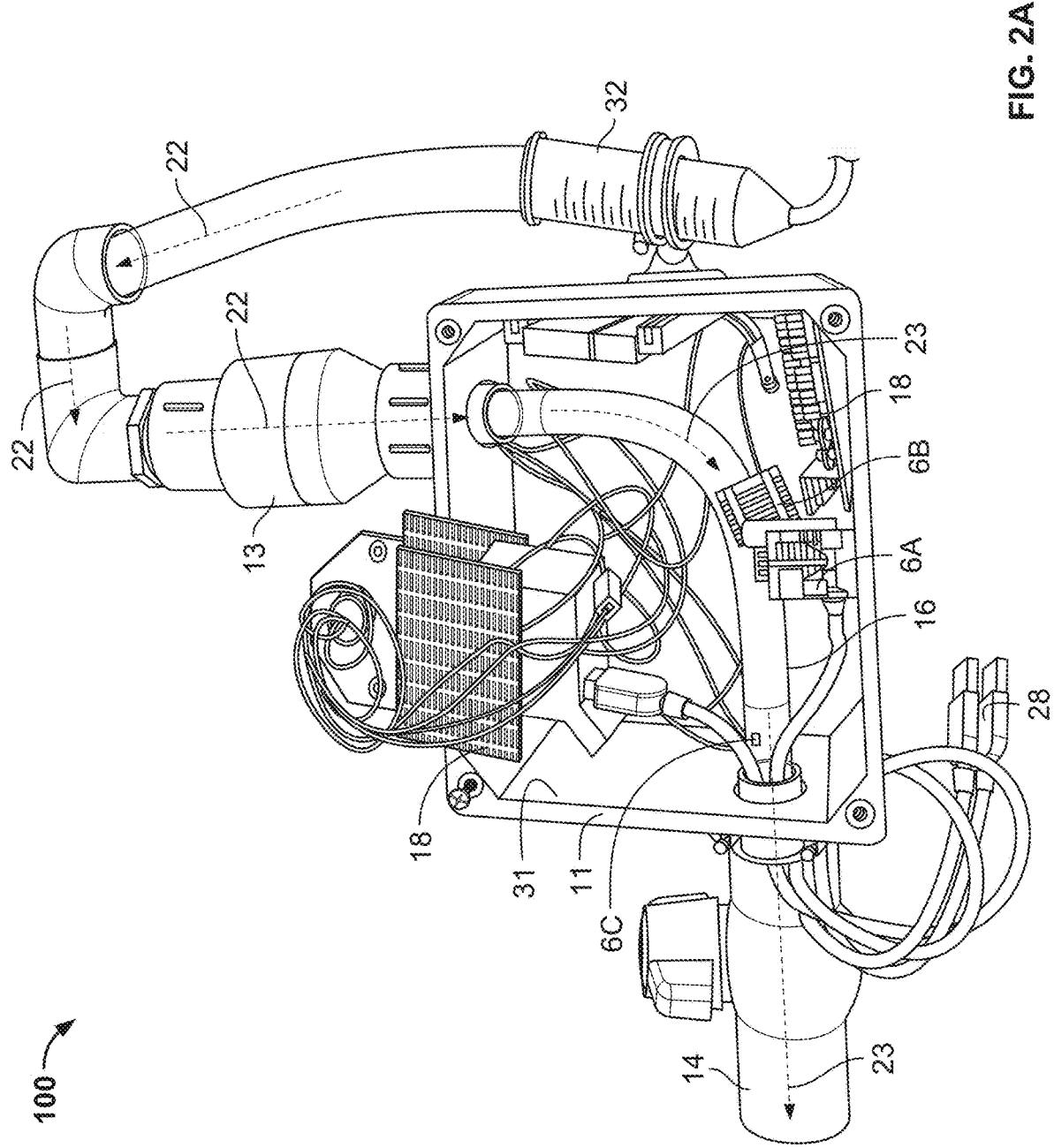
FIG. 2A is a cross-sectional view of the breath collection device.
Figure 2B:
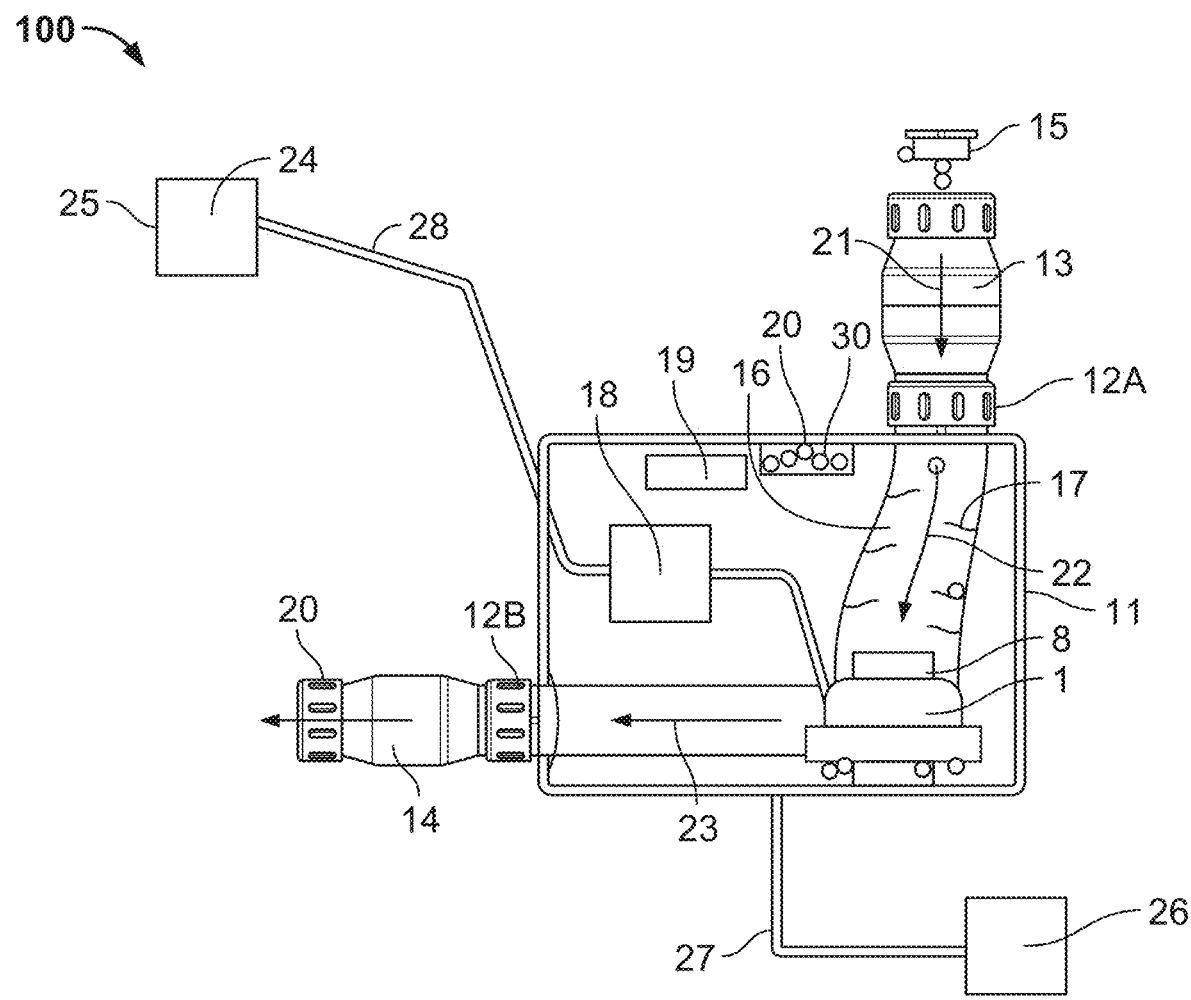
FIG. 2B is a schematic diagram of the breath collection device.

FIG. 2B is a schematic diagram of the breath collection device 100. In addition to the components described in reference to FIG. 2A, the breath collection device 100 includes a sensor 1 (e.g., one or more of the sensors 6A-C), a mucin gel layer 8, the mouth piece 15, projections 17 along the internal bladder 16, a UV lamp 19, a filtration system 20, air compressor hose 27, compressed air device 26, a mucus dispensing mechanism 29, and mucus 30. The breath collection device 100 can also be in communication with a computer 24 and a database 25. The device 100 can communicate with the computer 24 such that data collected by the sensors can be recorded (e.g., in the database 25) and used for subsequent analysis to determine a breath pattern signature of COVID-19.

The gas sensors (e.g., refer to the sensors 6A-C in FIG. 2A) can include the mucin gel layer 8. The layer 8 can be a replaceable insert overlaying the sensing elements and an optional heater element. For example, the layer 8 can be placed over the sensor 1 and/or the sensors 6A-C described in reference to FIG. 2A. The layer 8 can have a plurality of pores to allow passage of breath to pass through and communicate with the gas sensors. The layer 8 may not be static and can include cilia-like projections 17 coated in mucin gel 30. The projections 17 can be located on at least a portion of an interior wall surface of the internal bladder 16. The cilia-like projections 17 can move as force of the user's breath passes through the pores of the mucin gel layer 8, thereby mimicking a moist environment of a nasal cavity. This configuration of the projections 17 can be advantageous to increase selectivity and accuracy of the gas sensors towards the target gasses.

In some implementations, the mucus dispensing mechanism 29 can be configured to expel predetermined quantities of the mucus 30 within the internal bladder 16. The mucus 30 can be dispensed inside the bladder 16 while breath flows 21 through the first check valve 13 and/or flows 22 through the internal bladder 16. The mucus 30 can be dispensed to cover at least a portion of the cilia-like projections 17 and/or an internal wall surface of the internal bladder 16.

The UV lamp 19 (e.g., UVC light emitting diodes) can be configured to expose components within the chamber 31 of the housing 11 to UV light after the breath flows 23 out through the second check valve 14. Germicidal UV LEDs can kill bacteria within the chamber 31. Exposure to UV light can be advantageous to eliminate any of the breath that may still remain within the internal bladder 16. Thus, the UV lamp 19 can be used to sterilize the components within the chamber 31 of the housing 11 so that the breath collection device 100 can be used for a next breath sample. Moreover, if a user opens the housing 11 to service any one or more of the components within the chamber 31, the UV lamp 19 can be automatically turned off such that the user is not exposed to germicidal arrays.

Additional sterilization elements include the filtration system 20 can also be used to filter out the breath as it flows 23 from the internal bladder out through the second check valve 14. The filtration system 20 can also provide for purifying air is it is purged from the internal bladder 16. Moreover, as described in reference to FIG. 8, compressed air can be injected into the breath collection device 100 via the air compressor hose 27 in order to purge the components within the chamber 31 of the housing 11 from any remaining breath. The compressed air can be delivered from the compressed air device 25, through the hose 27, and into the internal bladder 16. The injected compressed air can then push any remaining breath out through the second check valve 14.

In some implementations, although not depicted, the breath collection device 100 can include a light emitting diode (LED) that can indicate detection of gas concentrations associated with COVID-19. For example, carbon monoxide emitted from a non-COVID-19 breath sample can have a concentration range between 2 ppm-100 ppm, corresponding to a "healthy" signature. When the sensor 1 (e.g., the MQ-2 sensor described herein) detects a concentration value of carbon monoxide emitted from the breath having a value over 100 ppm, a red LED of the breath collection device 100 can illuminate to indicate a potential inflammatory response symptom of COVID-19.

As another example, alcohol emitted from a non-COVID-19 breath sample can have a concentration range between 0.4 ppm-2.0 ppm, corresponding to a "healthy" signature. When the sensor 1 (e.g., the MQ-2 sensor) detects a value of alcohol emitted from the breath having a value over 2.0 ppm, a green LED of the breath collection device 100 can illuminate to indicate a potential inflammatory response symptom of COVID-19. Further, the sensor 1 can also be configured to detect a concentration of acetone (e.g., the MQ-135 sensor described herein). Acetone emitted from a non-COVID-19 breath sample can have a concentration range between 0.24 ppm-1.69 ppm, corresponding to a "healthy" signature. When the sensor 1 detects a concentration value of acetone emitted from the breath having a value over 2.0 ppm, a yellow LED can illuminate to indicate a potential inflammatory response symptom of COVID-19. Thus, if target gas concentrations in the breath exceed threshold values of at least 2 gas sensors (e.g., refer to the sensors 6A-C in FIG. 2A), this can be a strong indication of presence of an inflammatory response associated with COVID-19.

Figure 3:
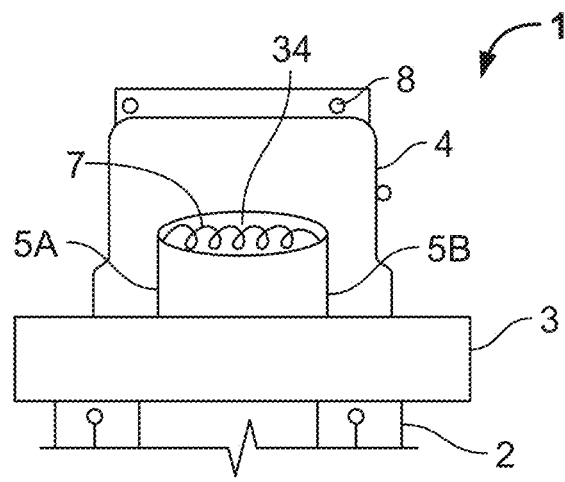
FIG. 3 is a schematic diagram of an example sensor in the breath collection device.

FIG. 3 is a schematic diagram of an example sensor 1 in the breath collection device 100. As described herein, the sensor 1 can be any one or more of the sensors 6A-C described throughout this document. For example, the sensor 1 can be a gas sensor, such as the MQ-2 and/or MQ-135 sensors described herein. The sensor 1 can also be a temperature-pressure sensor. The sensor 1 includes at least one tube pin 2, a clamp ring 3, a support structure 4, connecting legs 5A-B, a sensing element 34, a coil 7, and the mucin gel layer 8. As described herein, the sensor 1 can be positioned at least partially within the internal bladder 16. The sensor can also be positioned within the chamber 31 of the housing 11.

Figure 4:
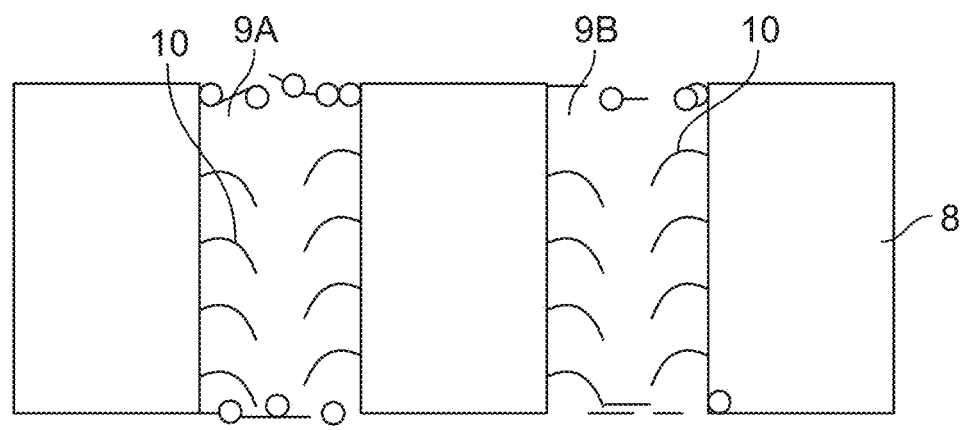
FIG. 4 is a schematic diagram of an example mucin gel layer of the breath collection device.

FIG. 4 is a schematic diagram of an example mucin gel layer 8 of the breath collection device 100. As described herein, the sensor 1 (e.g., a gas sensor) can include the mucin gel layer 8. The mucin gel layer 8 can include pores 9A-B for cilia-like projections 10 to radiate from. This configuration can mimic a nasal cavity of a user.

In some implementations, the mucin gel can be an electroconductive hydrogel derived from jelly of Ampullae of Lorenzini. Sharks, rays and skates have electro-sensing organs known as the Ampullae of Lorenzini, which can be characterized as a plurality of pores retaining a jelly-like substance. This proton conductive jelly can include glycosaminoglycan (GAG), keratin sulfate (KS), and mucin polyanions. This jelly can be used by the aforementioned elasmobranch fish to receive electric field signals generated by muscle contractions of other fish during hunting. This jelly can also include proteins such as calreticulin, which are responsible for regulating flow of calcium and potassium through membrane pores which influence electroreception. Mucin gels are involved in biological cell signaling in that they have a high binding affinity for growth factors and cytokines, which can be crucial in migration of MSCs. In particular, an electroconductive hydrogel derived from the jelly of Ampullae of Lorenzini can be a suitable cell culture substrate for application of electrical stimulation. This hydrogel can therefore be used to increase sensitivity and accuracy of the sensing element 34 of the sensor 1.

Figure 5:
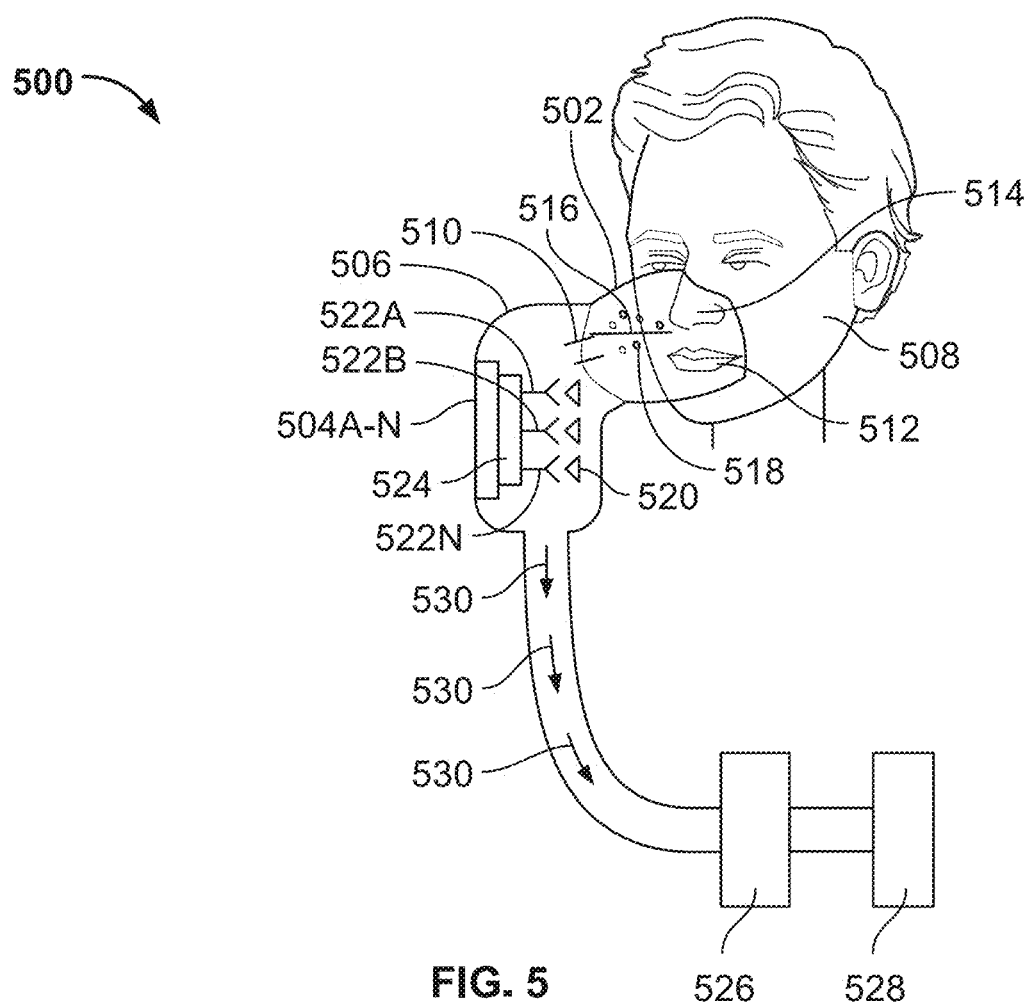
FIG. 5 is another example embodiment of a breath collection device.

FIG. 5 is another example embodiment of a breath collection device 500. The device 500 can include a dual chamber facemask 502, sensors 504A-N, a chamber 506, an intake port 510, a divider 516, aerosol 518, receptors 522A-N, mucin gel layer 524, and a detector 526. The device 500 can also be in communication with a computing device 528, as described in reference to the device 100. User 508 can place their mouth 512 and nose 514 within the dual chamber facemask 502 and exhale. The aerosol 518 can be injected within the dual chamber facemask 502 The user 508's breath can travel through the port 510 and into the chamber 506. The port 510 can be a one-way valve. Moreover, the divider 516 can be configured to prevent the breath from moving into the chamber 506 by any means other than the port 510.

The breath can flow 530 through the chamber 506 and past the receptors 522A-N and mucin gel layer 524. The mucin gel layer 524 can be configured to mimic a nasal cavity of the user 508, as described above. The gel layer 524 can include a mucin-based gel, shark gel, and/or antibodies. The receptors 522A-N can be configured to receive pathogen 520 in the user's breath. Once the pathogen 520 is received by the receptors 522A-N, the sensors 504A-N can detect gas concentrations associated with the pathogen 520 (e.g., refer to the sensor 1 and sensors 6A-C discussed throughout this disclosure).

The user's breath can flow 530 through the detector 526 and be expelled out of the device 100. Moreover, as described herein, the collection device 100 can communicate with the computing device 528 to perform analysis on the sensed concentrations of gasses.

Figure 6:
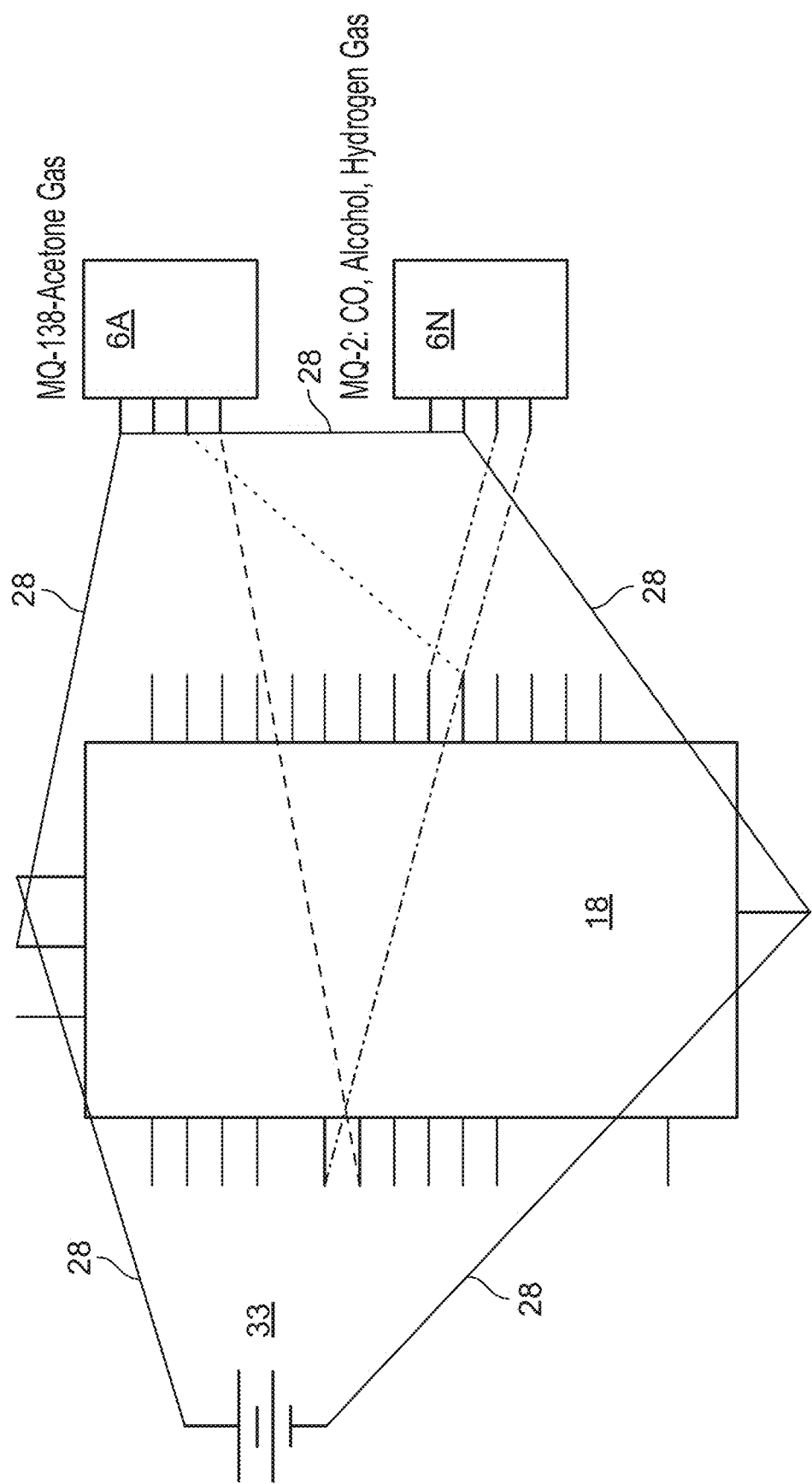
FIG. 6 depicts electrical communication of one or more components of the breath collection device.

FIG. 6 depicts electrical communication of one or more components of the breath collection device 100. As mentioned throughout this disclosure, the circuitry 18 can include the microcontroller. The microcontroller can be in electrical communication 28 with sensors 6A-N as well as a power source 33. Digital signals of the sensed gasses can be transmitted to the microcontroller (e.g., from the sensors 6A-N). The microcontroller can then convert the digital signals from output response (V) into concentration (ppm) based on the resistance ratio ($R_S/R_O$) of the resistance change when the sensors 6A-N are exposed to a target gas ($R_S$) in relation to a stable sensor resistance of the sensors 6A-N in clean air ($R_O$).

Moreover, the sensors 6A-N can be in electrical communication 28 with each other and the power source 33. The power source 33 can be a 5V battery. The power source 33 can also be a power source of another device or system, such as a computer that is in communication with the breath collection device 100.

Figure 7A:
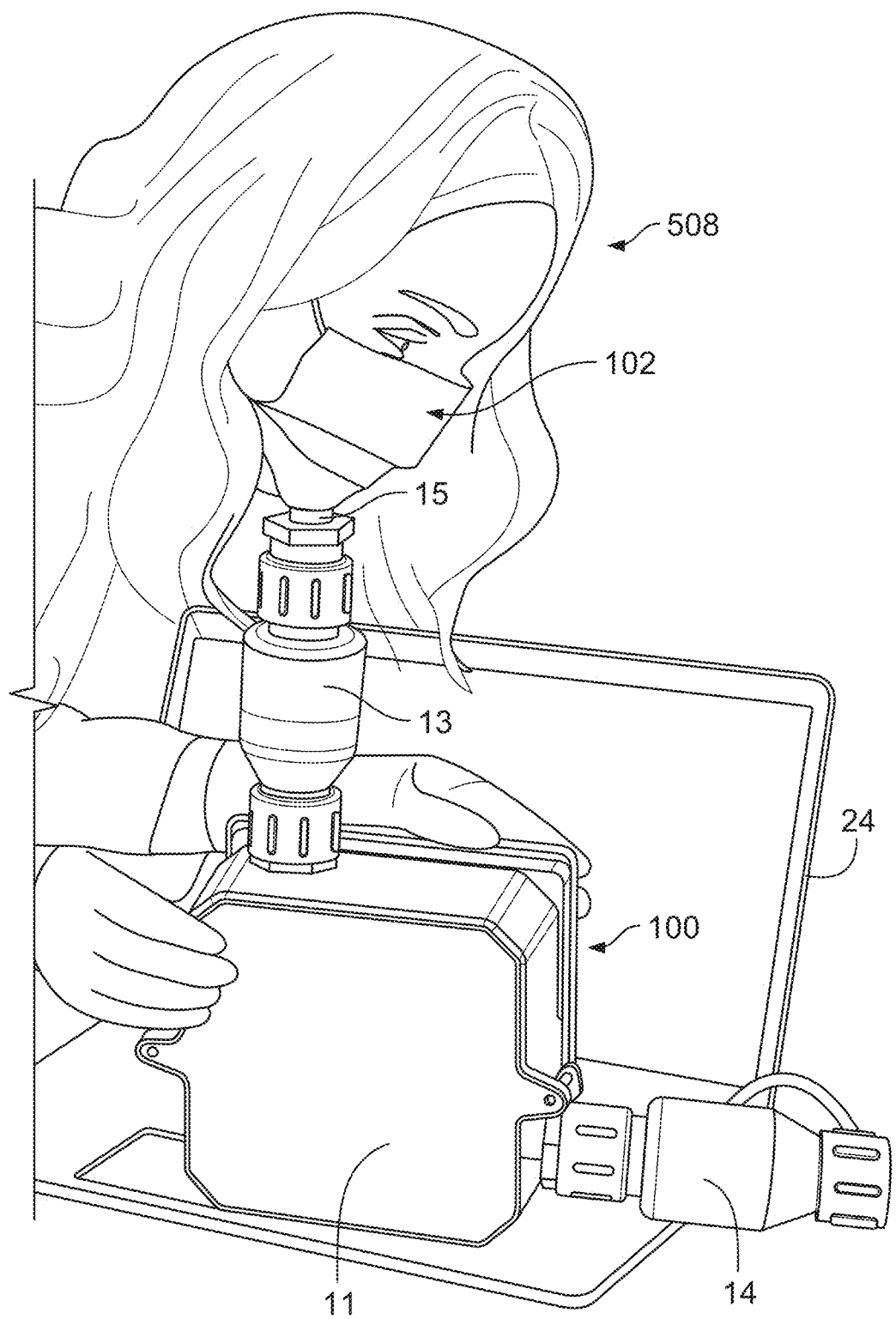
FIG. 7A depicts a user breathing into the breath collection device with a facemask.

FIG. 7A depicts a user 508 breathing into the breath collection device 100 with a facemask 102. In this example, the facemask 102 is configured with the mouthpiece 15. The user 508 breathes into the mouthpiece 15. The user's breath travels through the first check valve 13, through the chamber within the housing 11, and out through the second check valve 14. Data can be sensed by the sensors within the chamber, as described above. The sensed data can be transmitted (e.g., via wired and/or wireless communication) to the computer 24 for further analysis and processing.

The user 508 can be presented with user interfaces at the computer 24. The user interfaces 24 can allow the user 508 to calibrate the breath collection device 100. When calibration is complete, sensed gas concentrations can be outputted at the user interface. The user 508 can save the sensed gas concentrations (e.g., in a database) for further processing and analysis.

Figure 7B:
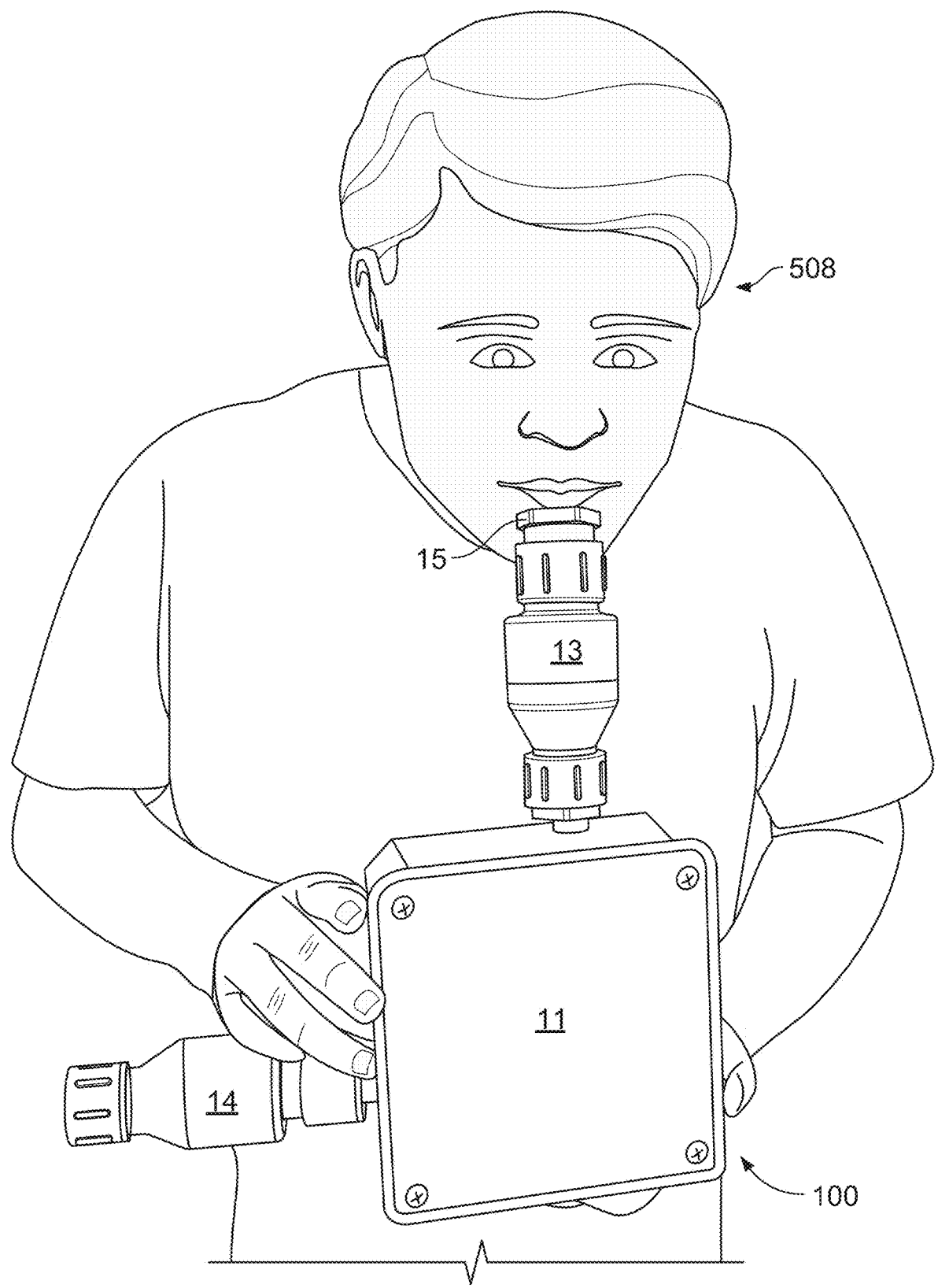
FIG. 7B depicts a user breathing directly into the breath collection device.

FIG. 7B depicts the user 508 breathing directly into the breath collection device 100. In this example, the user 508 breathes directly through the mouthpiece 15, which is attached to the first check valve 13 of the breath collection device 100.

FIG. 8 depicts a sterilization procedure for the breath collection device 100. After a breath sample is expelled from the device 100, the device 100 can be sterilized so that it can be used for a subsequent breath sample. To sterilize, the air compressor hose 27 can attach the breath collection device 100 to the compressed air device 26 via the mouthpiece 15. In some implementations, the mouthpiece 15 can be replaced with a reducer bushing that is sized from 1" to ½". In between uses of the device 100, the housing 11 can be purged with compressed air by squeezing a handle of the compressed air device 26 while the hose 27 is attached to the mouthpiece 15. The handle can be squeezed for 5 seconds. Any remaining breath within the housing 11 can be expelled though the second check valve 14 with this purging process.

As described herein, additional sterilization procedures can be performed. For example, the mouthpiece 15 can be sanitized and/or replaced for each user. UVC germicidal LEDs can be activated within the chamber of the housing 11 to remove any remaining bacteria therein. A filtration system can also be connected to the second check valve 14 to filter purged air out of the chamber within the housing 11.

Figure 9:
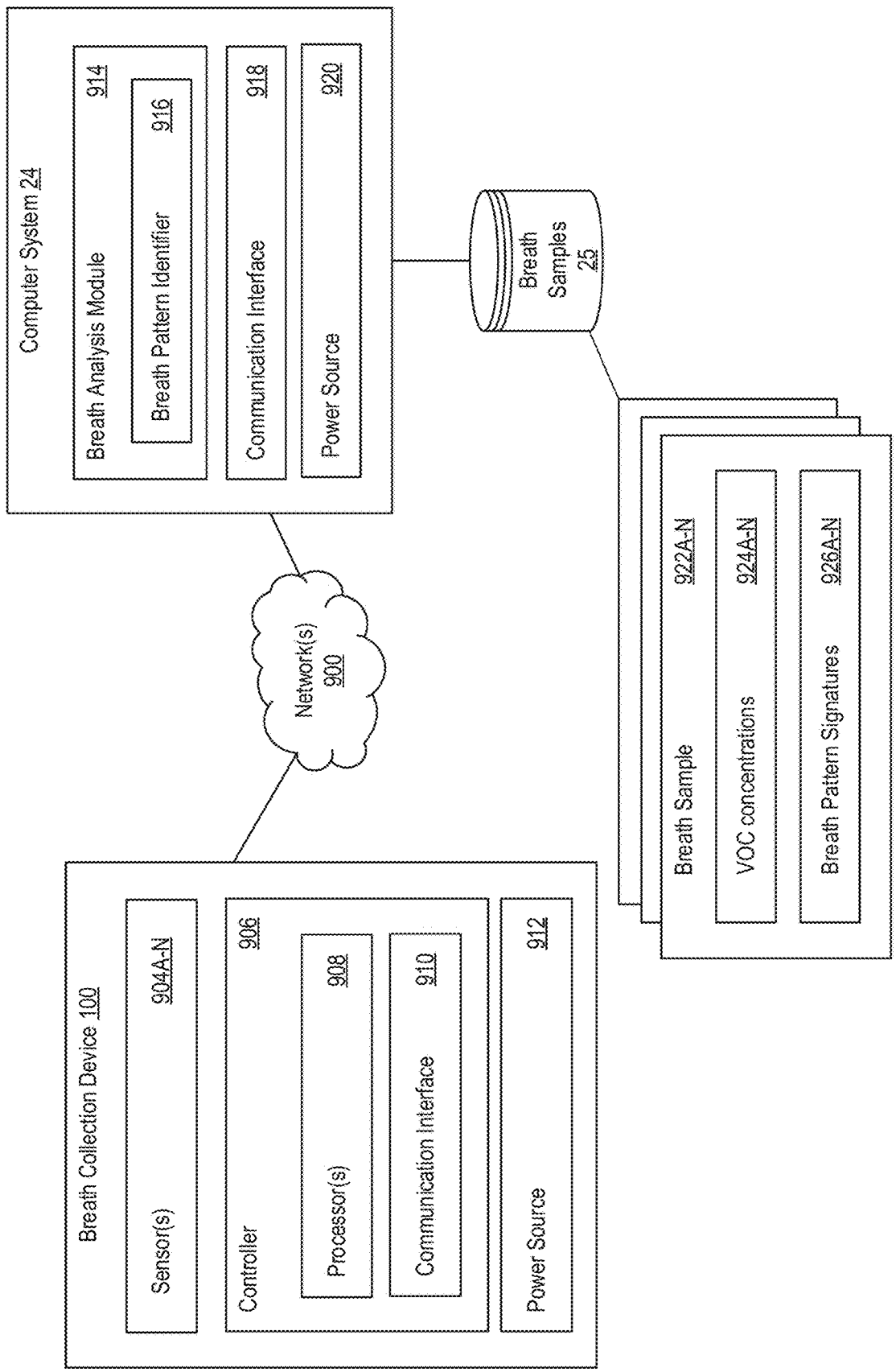
FIG. 9 is a system diagram of one or more components used to perform the techniques described herein.

FIG. 9 is a system diagram of one or more components used to perform the techniques described herein. The breath collection device 100 can communicate with the computer system 24 and the database 25 via network(s) 900.

The breath collection device 100, as described throughout this disclosure, can have one or more components. Some of the components can include but are not limited to sensor(s) 904A-N, a controller 906, and a power source 912. The sensors 904A-N can be any one or more of the gas, temperature, and/or pressure sensors described herein. The controller 906 can include processor(s) 908 and a communication interface 910. The processor(s) 906 can be configured to execute any one or more of the operations described herein. The communication interface 910 can provide for communication between the components of the breath collection device 100 and one or more of the other components described herein. The power source 912 can be a battery or other rechargeable source. In some implementations, the breath collection device 100 can include wiring that couples the device 100 to the computer system 24. The breath collection device 100 can then be powered by a power source of the computer system 24.

The computer system 24, as described throughout this disclosure, can have one or more components. Some of the components can include but are not limited to a breath analysis module 914, a communication interface 918, and a power source 920. The breath analysis module 914 can be a mobile application or other software interface that can be presented to a user. The module 914 can provide the user with functionality to collect breath samples from users. The module 914 can also provide the user with functionality to view gas concentrations within the collected breath samples. Moreover, the module 914 can provide the user with functionality to view information indicative of whether the collected breath samples are indicative of a disease or other condition. The breath analysis module 914 can also include a breath pattern identifier 916. The identifier 916 can be configured to determine VOC concentrations. The identifier 916 can also determine breath pattern signatures, which can indicate whether the breath sample is indicative of a disease or other condition. Once the identifier 916 determines information about the breath sample, the identified information can be stored in the database 25.

In the example of FIG. 9, the database 25 can store breath samples. The database 25 can also store a variety of other types of information related to the breath samples. An example stored breath sample 922A-N can include VOC concentrations 924A-N and breath pattern signatures 926A-N.

Still referring to the computer system 24, the communication interface 918 can provide for communication between components of the computer system 24 and other components described herein. The power source 920 can provide power to the computer system 24 and optionally to the breath collection device 100 as well. The power source 920 can be a battery or similar rechargeable power source.

Figure 10A:
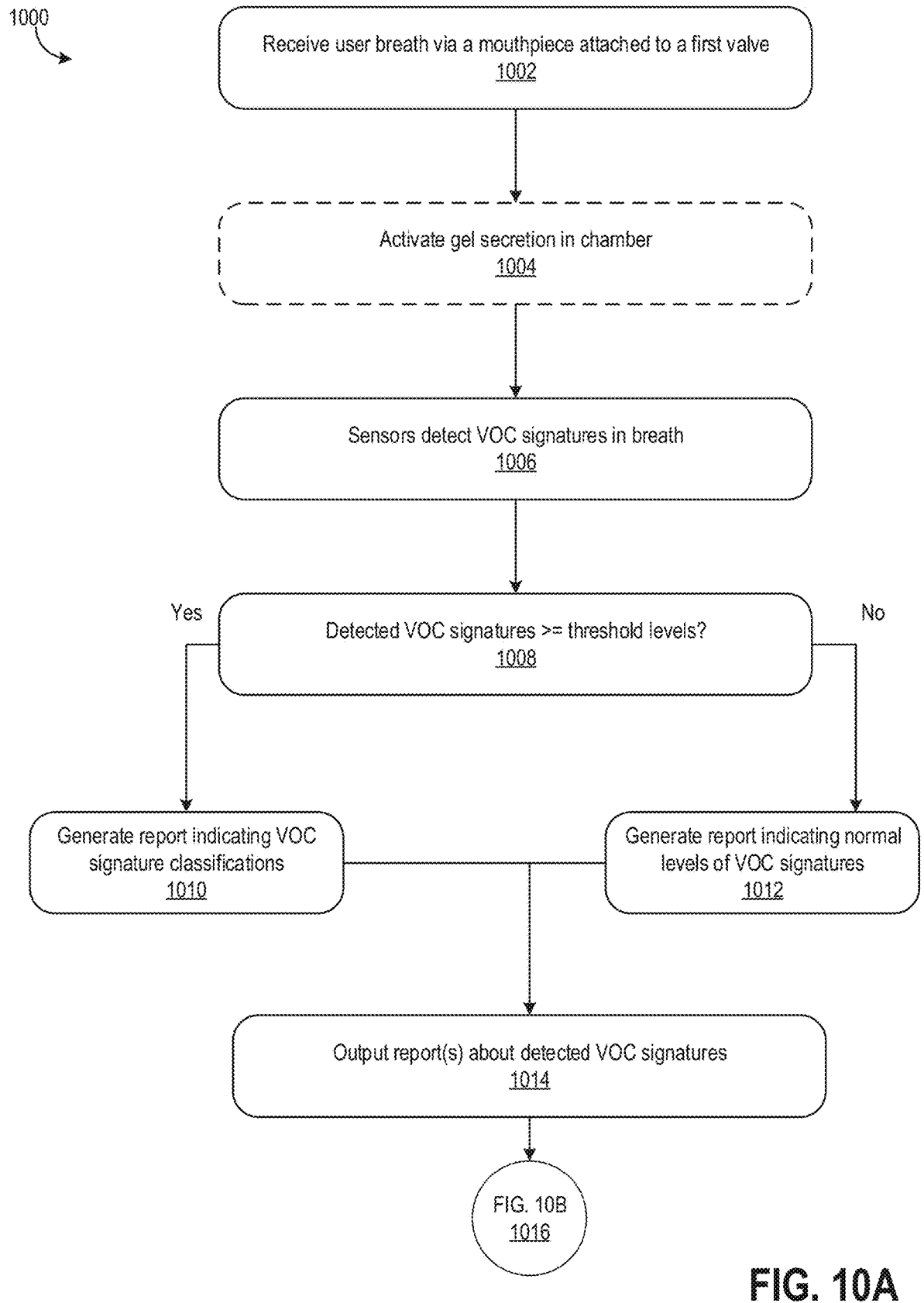
FIGS. 10A-B depict a flowchart of a process for using the breath collection device.
Figure 10B:
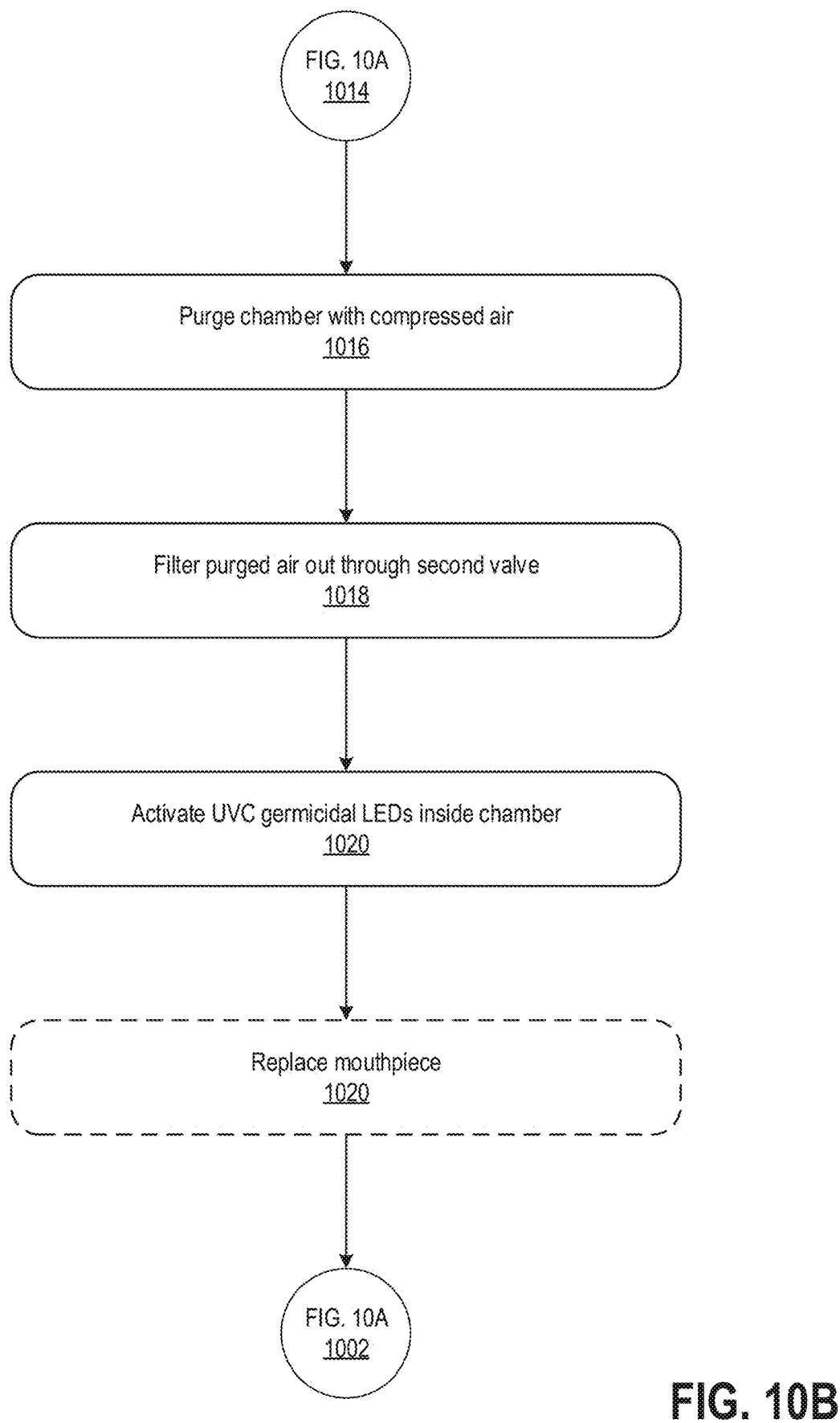

FIGS. 10A-B depict a flowchart of a process 1000 for using the breath collection device described herein. Referring to the process 1000 in both FIGS. 10A-B, user breath can be received via a mouthpiece that is attached to a first valve of the breath collection device (1002). As described herein, the mouthpiece can be configured to a facemask worn by the user. The user can then breathe through the mouthpiece and into the first valve of the collection device. The mouthpiece can also be configured directly to the first valve of the collection device.

Optionally, gel secretion can be activated within a chamber in a housing of the breath collection device (1004). The gel secretion can occur automatically once the breath is received within the chamber of the breath collection device. Mucin gel can be secreted within the chamber. As described herein, mucin gel is involved in biological cell signaling since the gel has a high binding affinity for growth factors and cytokines. Cytokines are byproducts of inflammation, and COVID invokes many cytokines. The mucin gel can therefore mimic a biological nasal passage, which can increase accuracy and selectivity of sensor in the collection device for a target gas.

Sensors within the breath collection device can detect VOC signatures in the breath as the breath travels through the device in 1006. The techniques described above can be used to detect the VOC signatures. The detected VOC signatures can be communicated to a computer system as described herein.

The computer system can then determine whether the detected VOC signatures are greater than or equal to predetermined threshold levels in 1008. The predetermined threshold levels can be used to indicate whether the breath sample is indicative of a disease or condition such as COVID-19. If the detected VOC signatures exceed the threshold levels, then a report can be generated indicating the VOC signature classifications in 1010. For example, the report can indicate which VOC signatures had high concentrations and what the high concentrations may be classified as. For example, the report can demonstrate that the breath sample as high concentrations of gases indicative of COVID-19. If the detected VOC signatures do not exceed the threshold levels, then a report can be generated indicating normal levels of VOC signatures in 1012. In other words, the breath sample is not indicative of a disease or condition such as COVID-19.

Next, the report(s) about detected VOC signatures can be outputted in 1014. The report(s) can be outputted to a display screen of the computer system described herein. The report(s) can also be outputted to any one or more devices of a user, such as a cell phone, mobile device, tablet, laptop, or computer.

Once the breath sample collection is completed (e.g., the sensors detect VOC concentrations), the chamber within the device can be purged with compressed air in 1016. As described herein, a compressed air device can be attached to the first valve of the device such that the compressed air can be injected therein. The compressed air can then push any remaining breath in the chamber out through a second valve in the device.

The purged air can be filtered out through the second valve in the device in 1018. A filtration system can be attached to the second valve, as described herein.

UVC germicidal LEDs can also be activated within the chamber of the collection device in 1020. As described herein, the LEDs can be automatically activated to kill any remaining bacteria that may exist within the chamber from the collected breath sample. In some implementations, if a user opens the collection device to access components therein, the LEDs can be configured to automatically deactivate. Thus, the user may not become exposed to the germicidal LEDs.

Optionally, the mouthpiece can be replaced in 1020. In some implementations, the mouthpiece can be sanitized. A new mouthpiece can be attached to the first valve. The mouthpiece may not need to be replaced in situations where the user breathes through a facemask having the mouthpiece attached thereto.

The process 1000 can then be repeated. The process 1000 can be repeated for each user whose breath is being tested.

Figure 11:
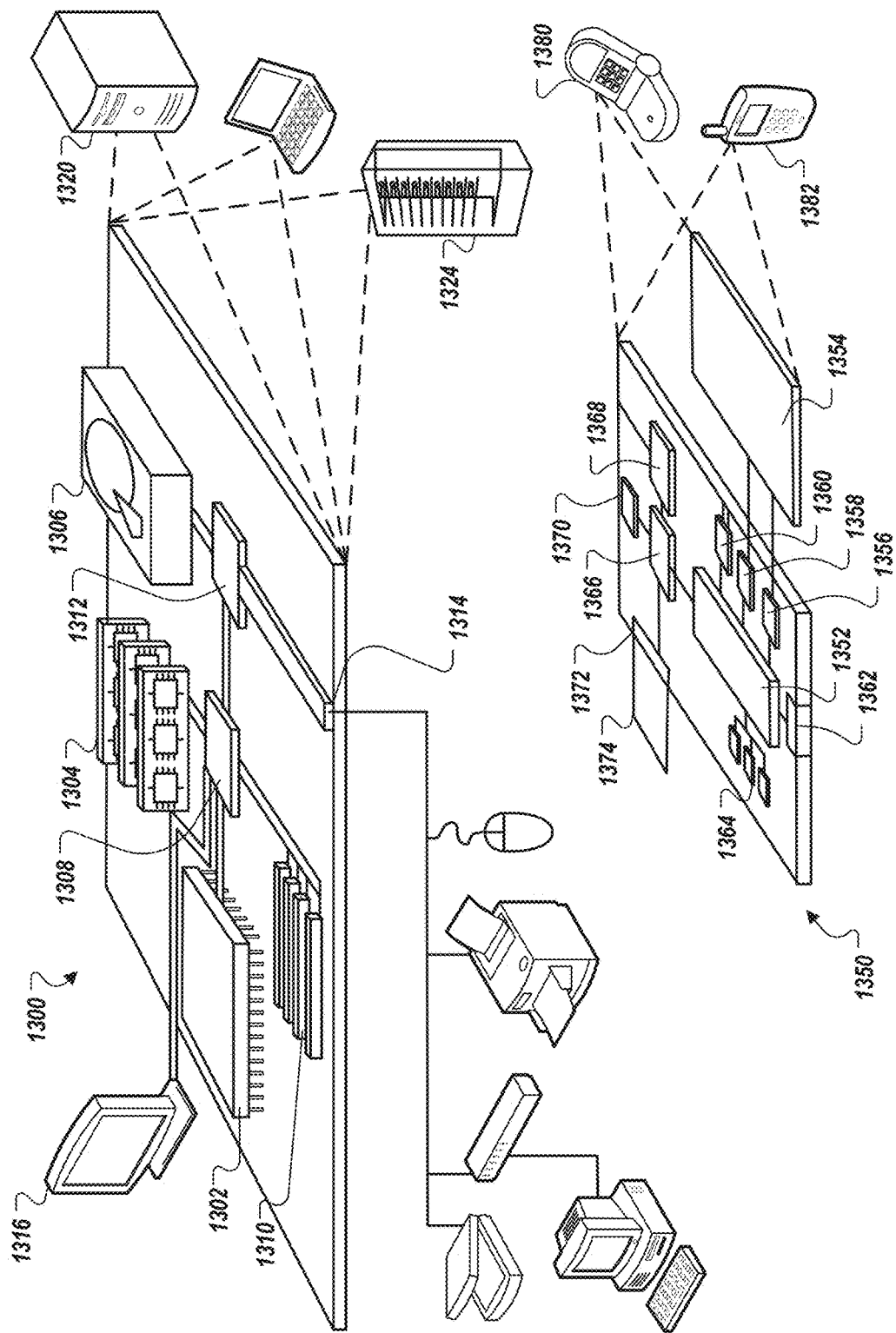
FIG. 11 is a schematic diagram that shows an example of a computing device and a mobile computing device.

FIG. 11 is a schematic diagram that shows an example of a computing device 1300 and a mobile computing device that can be used to implement the techniques described here. The computing device 1300 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 1300 includes a processor 1302, a memory 1304, a storage device 1306, a high-speed interface 1308 connecting to the memory 1304 and multiple high-speed expansion ports 1310, and a low-speed interface 1312 connecting to a low-speed expansion port 1314 and the storage device 1306. Each of the processor 1302, the memory 1304, the storage device 1306, the high-speed interface 1308, the high-speed expansion ports 1310, and the low-speed interface 1312, are interconnected using various busses, and can be mounted on a common motherboard or in other manners as appropriate. The processor 1302 can process instructions for execution within the computing device 1300, including instructions stored in the memory 1304 or on the storage device 1306 to display graphical information for a GUI on an external input/output device, such as a display 1316 coupled to the high-speed interface 1308. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 1304 stores information within the computing device 1300. In some implementations, the memory 1304 is a volatile memory unit or units. In some implementations, the memory 1304 is a non-volatile memory unit or units. The memory 1304 can also be another form of computer-readable medium, such as a magnetic or optical disk.

The storage device 1306 is capable of providing mass storage for the computing device 1300. In some implementations, the storage device 1306 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 1304, the storage device 1306, or memory on the processor 1302.

The high-speed interface 1308 manages bandwidth-intensive operations for the computing device 1300, while the low-speed interface 1312 manages lower bandwidth-intensive operations. Such allocation of functions is exemplary only. In some implementations, the high-speed interface 1308 is coupled to the memory 1304, the display 1316 (e.g., through a graphics processor or accelerator), and to the high-speed expansion ports 1310, which can accept various expansion cards (not shown). In the implementation, the low-speed interface 1312 is coupled to the storage device 1306 and the low-speed expansion port 1314. The low-speed expansion port 1314, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 1300 can be implemented in a number of different forms, as shown in the figure. For example, it can be implemented as a standard server 1320, or multiple times in a group of such servers. In addition, it can be implemented in a personal computer such as a laptop computer 1322. It can also be implemented as part of a rack server system 1324. Alternatively, components from the computing device 1300 can be combined with other components in a mobile device (not shown), such as a mobile computing device 1350. Each of such devices can contain one or more of the computing device 1300 and the mobile computing device 1350, and an entire system can be made up of multiple computing devices communicating with each other.

The mobile computing device 1350 includes a processor 1352, a memory 1364, an input/output device such as a display 1354, a communication interface 1366, and a transceiver 1368, among other components. The mobile computing device 1350 can also be provided with a storage device, such as a micro-drive or other device, to provide additional storage. Each of the processor 1352, the memory 1364, the display 1354, the communication interface 1366, and the transceiver 1368, are interconnected using various buses, and several of the components can be mounted on a common motherboard or in other manners as appropriate.

The processor 1352 can execute instructions within the mobile computing device 1350, including instructions stored in the memory 1364. The processor 1352 can be implemented as a chipset of chips that include separate and multiple analog and digital processors. The processor 1352 can provide, for example, for coordination of the other components of the mobile computing device 1350, such as control of user interfaces, applications run by the mobile computing device 1350, and wireless communication by the mobile computing device 1350.

The processor 1352 can communicate with a user through a control interface 1358 and a display interface 1356 coupled to the display 1354. The display 1354 can be, for example, a TFT (Thin-Film-Transistor Liquid Crystal Display) display or an OLED (Organic Light Emitting Diode) display, or other appropriate display technology. The display interface 1356 can comprise appropriate circuitry for driving the display 1354 to present graphical and other information to a user. The control interface 1358 can receive commands from a user and convert them for submission to the processor 1352. In addition, an external interface 1362 can provide communication with the processor 1352, so as to enable near area communication of the mobile computing device 1350 with other devices. The external interface 1362 can provide, for example, for wired communication in some implementations, or for wireless communication in other implementations, and multiple interfaces can also be used.

The memory 1364 stores information within the mobile computing device 1350. The memory 1364 can be implemented as one or more of a computer-readable medium or media, a volatile memory unit or units, or a non-volatile memory unit or units. An expansion memory 1374 can also be provided and connected to the mobile computing device 1350 through an expansion interface 1372, which can include, for example, a SIMM (Single In Line Memory Module) card interface. The expansion memory 1374 can provide extra storage space for the mobile computing device 1350, or can also store applications or other information for the mobile computing device 1350. Specifically, the expansion memory 1374 can include instructions to carry out or supplement the processes described above, and can include secure information also. Thus, for example, the expansion memory 1374 can be provide as a security module for the mobile computing device 1350, and can be programmed with instructions that permit secure use of the mobile computing device 1350. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 1364, the expansion memory 1374, or memory on the processor 1352. In some implementations, the computer program product can be received in a propagated signal, for example, over the transceiver 1368 or the external interface 1362.

The mobile computing device 1350 can communicate wirelessly through the communication interface 1366, which can include digital signal processing circuitry where necessary. The communication interface 1366 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 1368 using a radio-frequency. In addition, short-range communication can occur, such as using a Bluetooth, WiFi, or other such transceiver (not shown). In addition, a GPS (Global Positioning System) receiver module 1370 can provide additional navigation- and location-related wireless data to the mobile computing device 1350, which can be used as appropriate by applications running on the mobile computing device 1350.

The mobile computing device 1350 can also communicate audibly using an audio codec 1360, which can receive spoken information from a user and convert it to usable digital information. The audio codec 1360 can likewise generate audible sound for a user, such as through a speaker, e.g., in a handset of the mobile computing device 1350. Such sound can include sound from voice telephone calls, can include recorded sound (e.g., voice messages, music files, etc.) and can also include sound generated by applications operating on the mobile computing device 1350.

The mobile computing device 1350 can be implemented in a number of different forms, as shown in the figure. For example, it can be implemented as a cellular telephone 1380. It can also be implemented as part of a smart-phone 1382, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

What is claimed is:

1. A breath collection system for sensing an infectious disease, the system comprising:
   a housing having a chamber located therein;
   a first check valve attached to the housing and in fluid communication with the chamber, wherein the first check valve is configured to receive a breath sample from a user; and
   a second check valve attached to the housing and in fluid communication with the chamber, wherein the second check valve is configured to expel the breath sample from the chamber,
   wherein the chamber houses:
      an internal bladder in fluid communication with the first check valve and the second check valve;
      a plurality of sensors positioned at least partially within the internal bladder, wherein the plurality of sensors are configured to detect one or more VOC signatures in the breath sample; and
      a microcontroller in electrical communication with the plurality of sensors, wherein the microcontroller is configured to classify, based on the detected VOC signatures in the breath sample, the breath sample.

2. The breath collection system of claim 1, further comprising at least one mucin gel layer configured to overlay at least one of the plurality of sensors, wherein the one mucin gel layer resembles a nasal cavity of a user.

3. The breath collection system of claim 2, wherein the at least one mucin gel layer includes a plurality of pores through which a plurality of synthetic hair-like projections radiate therefrom.

4. The breath collection system of claim 1, further comprising a plurality of synthetic hair-like projections that radiate from an inner wall surface of the internal bladder.

5. The breath collection system of claim 4, further comprising a mucus dispensing mechanism housed within the chamber, wherein the mucus dispensing mechanism is configured to inject a predetermined quantity of mucin-based gel into the chamber, wherein the mucin-based gel covers at least a portion of the plurality of synthetic hair-like projections and the inner wall surface of the internal bladder.

6. The breach collection system of claim 1, further comprising UVC germicidal LEDs housed within the chamber, wherein the UVC germicidal LEDs are configured to, when actuated, remove bacteria from within the internal bladder.

7. The breath collection system of claim 1, further comprising a filtration system attached to the second check valve and configured to purify air that is purged from within the internal bladder.

8. The breath collection system of claim 1, further comprising a compressed air device having a hose, wherein the hose is configured to attach to the first check valve and inject compressed air into the internal bladder.

9. The breath collection system of claim 1, further comprising a mouthpiece removably attached to and in fluid communication with the first check valve, wherein the mouthpiece is configured to receive a mouth of the user.

10. The breath collection system of claim 1, wherein at least one of the plurality of sensors is configured to detect gas concentrations in parts per million of at least one of carbon monoxide, acetone, or alcohol.

11. The breath collection system of claim 1, further comprising a facemask having a mouthpiece, wherein the facemask is worn by the user, wherein the mouthpiece is configured to receive breath from the user and wherein the mouthpiece is in fluid communication with the first check valve.

12. The breath collection system of claim 2, wherein the at least one mucin gel layer is an electroconductive hydrogel derived from jelly of Ampullae of Lorenzini.

13. A method for detecting VOC signatures indicative of an infectious disease in a breath sample, the method comprising:
   receiving the breath sample via a mouthpiece in fluid communication with a first check valve in a breath collection device;
   activating mucin-based gel secretion in a chamber housed within the breath collection device, wherein the mucin-based gel is configured to coat at least a portion of an interior wall surface of the chamber;
   detecting, by one or more sensors housed in the chamber, VOC signatures in the breath sample;
   classifying, based on the VOC signatures exceeding threshold levels, the breath sample as infected; and
   expelling the breath sample through a second check valve in the breath collection device.

14. The method of claim 13, further comprising:
   removing the mouthpiece from the first check valve;
   attaching an air compressor to the first check valve; and
   injecting compressed air from the air compressor into the chamber of the breath collection device, wherein the compressed air is configured to push the breath sample out through the second check valve in the breath collection device.

15. The method of claim 13, further comprising activating UVC germicidal LEDs within the chamber to remove bacteria from within the chamber.

16. A diagnostic system for sensing viruses, the diagnostic system comprising:
   a breath collection device having a housing, wherein the housing includes:
      at least a portion of a removable mask that is configured to overlay a mouth and a nose of a user;
      a collection element that is retained by a support structure of an inner wall surface of the removable mask portion;
      an intake pump configured to guide aerosols from the removable mask portion to the collection element;
      a pressure sensor in electrical communication with the intake pump;
      a gas sensor configured to detect gas concentrations in the aerosols; and
      a layer of porous film configured to overlay the gas sensor.

17. The diagnostic system of claim 16, wherein the collection element has an inner wall surface that includes at least a portion of a nanofilm having at least one receptor, wherein at least a portion of the nanofilm is magnetic.

18. The diagnostic system of claim 17, wherein the at least one receptor is at least one of (i) angiotensin-converting enzyme 2 and (ii) liver and lymph node sinusoidal endothelial cell c-type lectin.

19. The diagnostic system of claim 17, wherein a first receptor of the at least one receptor is angiotensin-converting enzyme 2 and a second receptor of the at least one receptor is liver and lymph node sinusoidal endothelial cell c-type lectin.

20. The diagnostic system of claim 16, wherein the layer of porous film is at least one of (i) an electroconductive hydrogel derived from jelly of Ampullae of Lorenzini and (ii) a mucin-based gel.

* * * * *